(12) United States Patent
Shashua et al.

(10) Patent No.: US 11,462,006 B2
(45) Date of Patent: Oct. 4, 2022

(54) SYSTEMS AND METHODS FOR MONITORING CONSUMPTION

(71) Applicant: ORCAM TECHNOLOGIES LTD., Jerusalem (IL)

(72) Inventors: Amnon Shashua, Mevaseret Zion (IL); Yonatan Wexler, Jerusalem (IL)

(73) Assignee: OrCam Technologies Ltd., Jerusalem (IL)

( * ) Notice: Subject to any disclaimer, the term of this patent is extended or adjusted under 35 U.S.C. 154(b) by 91 days.

(21) Appl. No.: 16/970,544

(22) PCT Filed: Feb. 14, 2019

(86) PCT No.: PCT/IB2019/000165
§ 371 (c)(1),
(2) Date: Aug. 17, 2020

(87) PCT Pub. No.: WO2019/159006
PCT Pub. Date: Aug. 22, 2019

(65) Prior Publication Data
US 2021/0110159 A1  Apr. 15, 2021

Related U.S. Application Data

(60) Provisional application No. 62/631,963, filed on Feb. 19, 2018.

(51) Int. Cl.
*G06K 9/00* (2022.01)
*G06V 20/10* (2022.01)
(Continued)

(52) U.S. Cl.
CPC ............. *G06V 20/10* (2022.01); *G06T 7/248* (2017.01); *G16H 20/60* (2018.01); *H04N 5/225* (2013.01)

(58) Field of Classification Search
CPC ...... G06K 9/00664; H04N 5/225; H04N 5/33; G16H 20/60; G06T 7/248; G06Q 20/4016;
(Continued)

(56) References Cited

U.S. PATENT DOCUMENTS

2016/0012749 A1* 1/2016 Connor .................... A61B 5/00
600/13

OTHER PUBLICATIONS

PCT International Search Report and Written Opinion of PCT Application PCT/IB2019/000165 filed Feb. 14, 2019 (12 pages).

* cited by examiner

*Primary Examiner* — Phuoc H Doan
(74) *Attorney, Agent, or Firm* — Finnegan, Henderson, Farabow, Garrett & Dunner, LLP

(57) ABSTRACT

A wearable apparatus may automatically monitor consumption by a user of the wearable apparatus by analyzing images captured from an environment of the user. The wearable apparatus may include at least one image capture device configured to capture a plurality of images from an environment of the user of the wearable apparatus. The wearable apparatus may also include at least one processing device configured to: analyze the plurality of images to detect a consumable product represented in at least one of the plurality of images; based on the detection of the consumable product represented in at least one of the plurality of images, analyze one or more of the plurality of images to determine a type indicator associated with the detected consumable product; analyze the one or more of the plurality of images to estimate an amount of the consumable product consumed by the user; determine a feedback based on the type indicator the detected consumable product and the estimated amount of the consumable product consumed by the user; and cause the feedback to be outputted to the user.

28 Claims, 28 Drawing Sheets

(51) Int. Cl.
*G06T 7/246* (2017.01)
*G16H 20/60* (2018.01)
*H04N 5/225* (2006.01)

(58) Field of Classification Search
CPC ...... G06Q 20/407; G06Q 20/10; G06F 16/22; G01N 21/8851
USPC .......................................... 382/181; 273/260
See application file for complete search history.

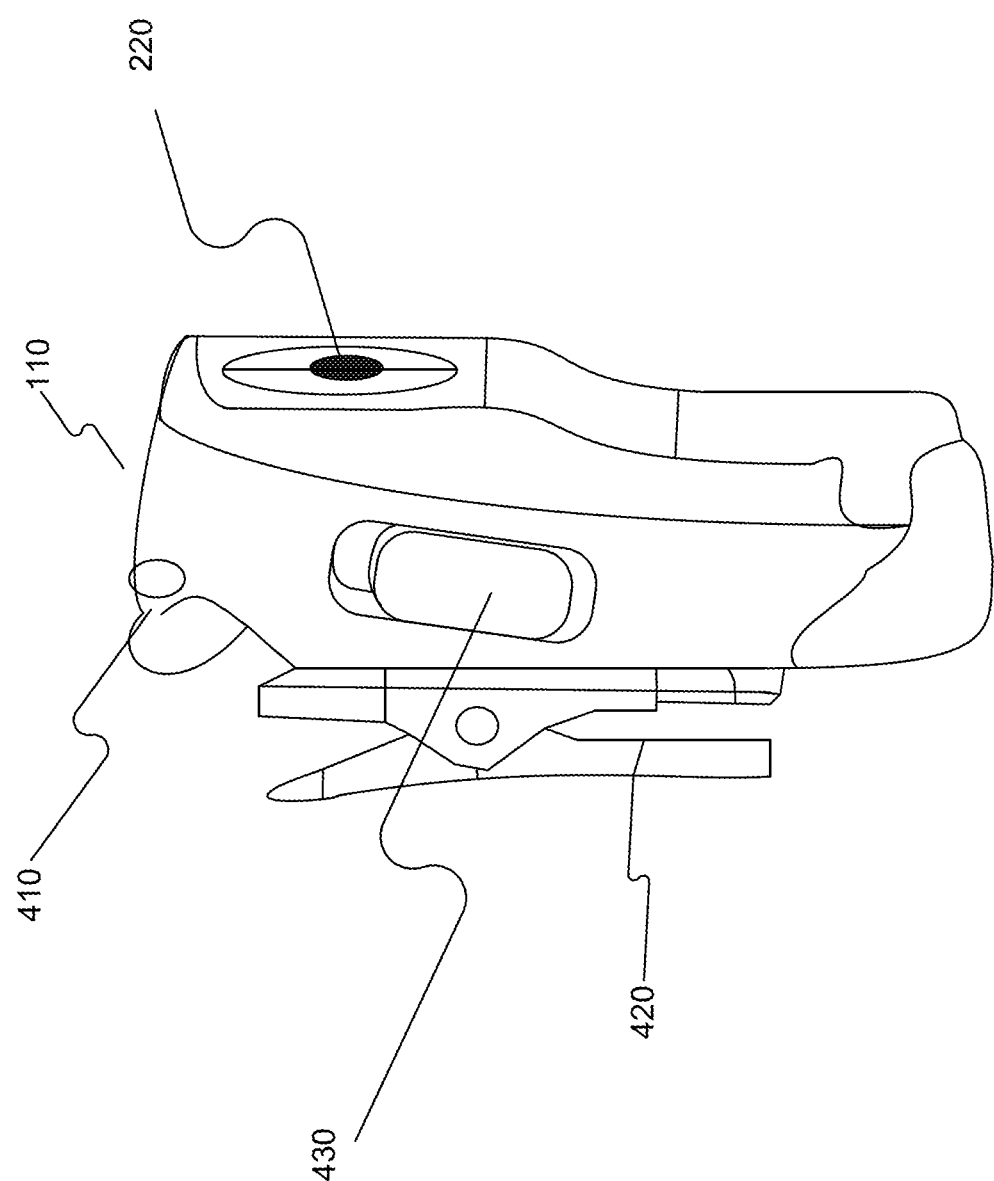

SYSTEMS AND METHODS FOR MONITORING CONSUMPTION

CROSS REFERENCES TO RELATED APPLICATIONS

This application is a national stage entry under 35 U.S.C. § 371 based on International Application No. PCT/IB2019/000165, filed Feb. 14, 2019, and claims the benefit of priority of U.S. Provisional Patent Application No. 62/631,963, filed Feb. 19, 2018. The contents of the aforementioned applications are incorporated herein by reference in their entirety.

BACKGROUND

Technical Field

This disclosure generally relates to devices and methods for capturing and processing images from an environment of a user, and using information derived from captured images.

Background Information

Today, technological advancements make it possible for wearable devices to automatically capture images and store information that is associated with the captured images. Certain devices have been used to digitally record aspects and personal experiences of one's life in an exercise typically called "lifelogging." Some individuals log their life so they can retrieve moments from past activities, for example, social events, trips, etc. Lifelogging may also have significant benefits in other fields (e.g., business, fitness and healthcare, and social research). Lifelogging devices, while useful for tracking daily activities, may be improved with capability to enhance one's interaction in his environment with feedback and other advanced functionality based on the analysis of captured image data.

Even though users can capture images with their smartphones and some smartphone applications can process the captured images, smartphones may not be the best platform for serving as lifelogging apparatuses in view of their size and design. Lifelogging apparatuses should be small and light, so they can be easily worn. Moreover, with improvements in image capture devices, including wearable apparatuses, additional functionality may be provided to assist users in navigating in and around an environment, identifying persons and objects they encounter, and providing feedback to the users about their surroundings and activities. Therefore, there is a need for apparatuses and methods for automatically capturing and processing images to provide useful information to users of the apparatuses, and for systems and methods to process and leverage information gathered by the apparatuses.

SUMMARY

Embodiments consistent with the present disclosure provide devices and methods for automatically capturing and processing images from an environment of a user, and systems and methods for processing information related to images captured from the environment of the user.

In an embodiment, a wearable apparatus may automatically monitor consumption by a user of the wearable apparatus by analyzing images captured from an environment of the user. The wearable apparatus may include at least one image capture device configured to capture a plurality of images from an environment of the user of the wearable apparatus; and at least one processing device configured to: analyze the plurality of images to detect a consumable product represented in at least one of the plurality of images; based on the detection of the consumable product represented in at least one of the plurality of images, analyze one or more of the plurality of images to determine a type indicator associated with the detected consumable product; analyze the one or more of the plurality of images to estimate an amount of the consumable product consumed by the user; determine a feedback based on the type indicator of the detected consumable product and the estimated amount of the consumable product consumed by the user; and cause the feedback to be outputted to the user.

In another embodiment, a method may automatically monitor consumption by a user of a wearable apparatus. The method may include capturing, by the wearable apparatus, one or more images from an environment of the user; analyzing the images to detect a consumable product represented in at least one of the one or more images; determining a type of the detected consumable product: analyzing the images to estimate an amount of the consumable product consumed by the user, determining a feedback based on the type of the consumable product and the amount of the consumable product consumed by the user: and generating instructions for causing the feedback to be output to the user.

Consistent with other disclosed embodiments, non-transitory computer-readable storage media may store program instructions, which are executed by at least one processor and perform any of the methods described herein.

The foregoing general description and the following detailed description are exemplary and explanatory only and are not restrictive of the claims.

The accompanying drawings, which are incorporated in and constitute a part of this disclosure, illustrate various disclosed embodiments. In the drawings:

FIG. 4B is a schematic illustration of the example of the wearable apparatus shown in FIG. 1B from a second viewpoint.

DETAILED DESCRIPTION

Figure 1A:
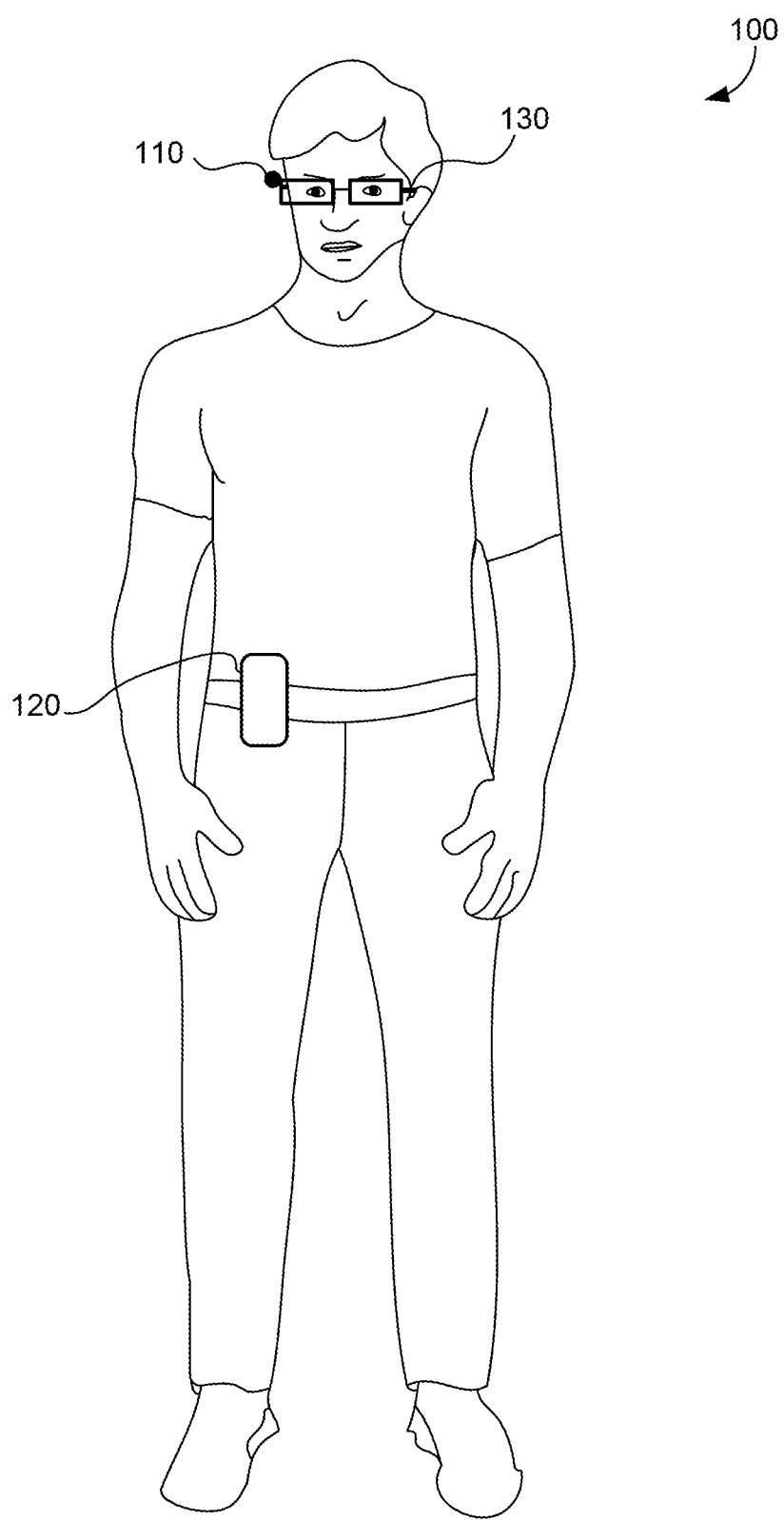
FIG. 1A is a schematic illustration of an example of a user wearing a wearable apparatus according to a disclosed embodiment.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

FIG. 1A illustrates a user 100 wearing an apparatus 110 that is physically connected (or integral) to glasses 130, consistent with the disclosed embodiments. Glasses 130 may be prescription glasses, magnifying glasses, non-prescription glasses, safety glasses, sunglasses, etc. Additionally, in some embodiments, glasses 130 may include pans of a frame and earpieces, nosepieces, etc., and one or no lenses. Thus, in some embodiments, glasses 130 may function primarily to support apparatus 110, and/or an augmented reality display device or other optical display device. In some embodiments, apparatus 110 may include an image sensor (not shown in FIG. 1A) for capturing real-time image data of the field-of-view of user 100. The term "image data" includes any form of data retrieved from optical signals in the near-infrared, infrared, visible, and ultraviolet spectrums. The image data may include video clips and/or photographs.

In some embodiments, apparatus 110 may communicate wirelessly or via a wire with a computing device 120. In some embodiments, computing device 120 may include, for example, a smartphone, or a tablet, or a dedicated processing unit, which may be portable (e.g., can be carried in a pocket of user 100). Although shown in FIG. 1A as an external device, in some embodiments, computing device 120 may be provided as part of wearable apparatus 110 or glasses 130, whether integral thereto or mounted thereon. In some embodiments, computing device 120 may be included in an augmented reality display device or optical head mounted display provided integrally or mounted to glasses 130. In other embodiments, computing device 120 may be provided as part of another wearable or portable apparatus of user 100 including a wrist-strap, a multifunctional watch, a button, a clip-on, etc. And in other embodiments, computing device 120 may be provided as part of another system, such as an on-board automobile computing or navigation system. A person skilled in the art can appreciate that different types of computing devices and arrangements of devices may implement the functionality of the disclosed embodiments. Accordingly, in other implementations, computing device 120 may include a Personal Computer (PC), laptop, an internet server, etc.

Figure 1B:
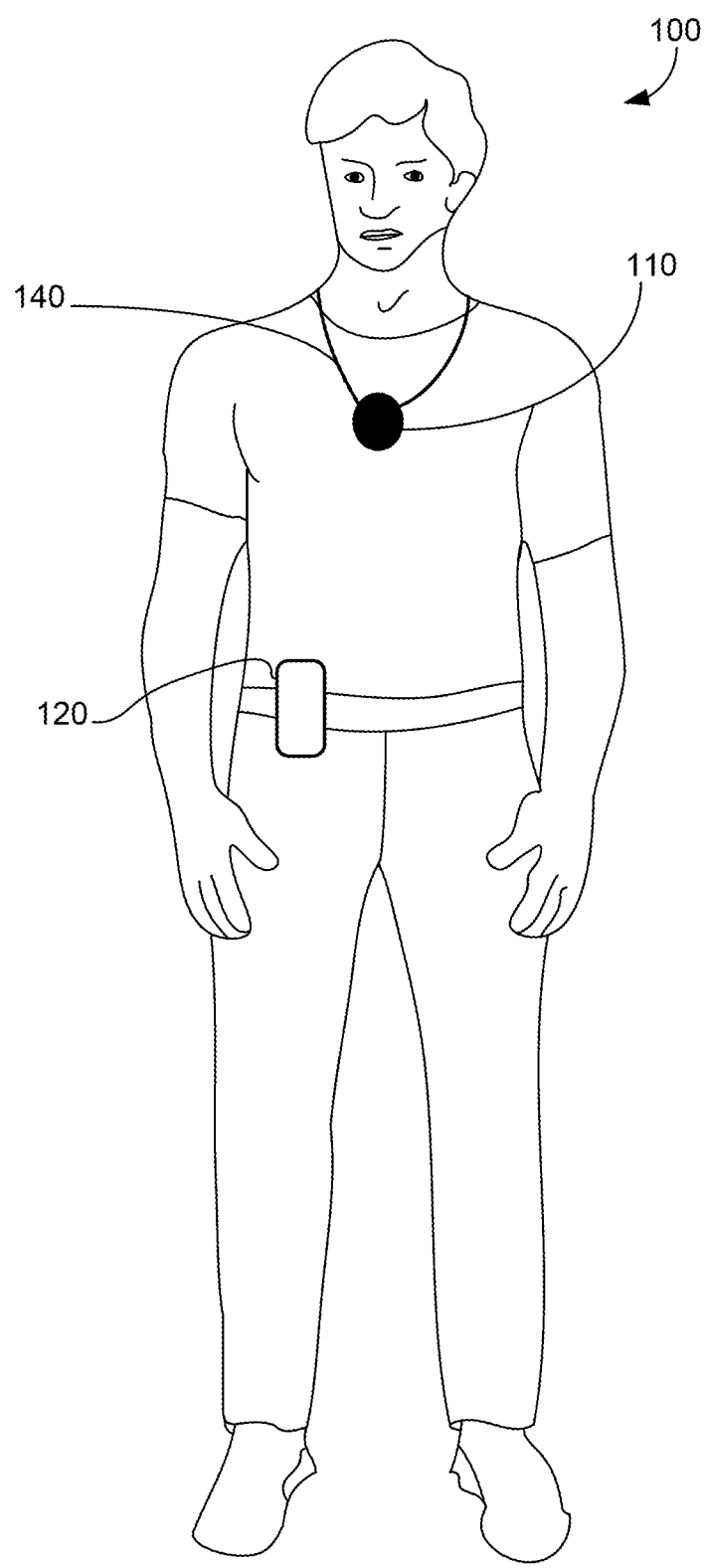
FIG. 1B is a schematic illustration of an example of the user wearing a wearable apparatus according to a disclosed embodiment.

FIG. 1B illustrates user 100 wearing apparatus 110 that is physically connected to a necklace 140, consistent with a disclosed embodiment. Such a configuration of apparatus 110 may be suitable for users that do not wear glasses some or all of the time. In this embodiment, user 100 can easily wear apparatus 110, and take it off.

Figure 1C:
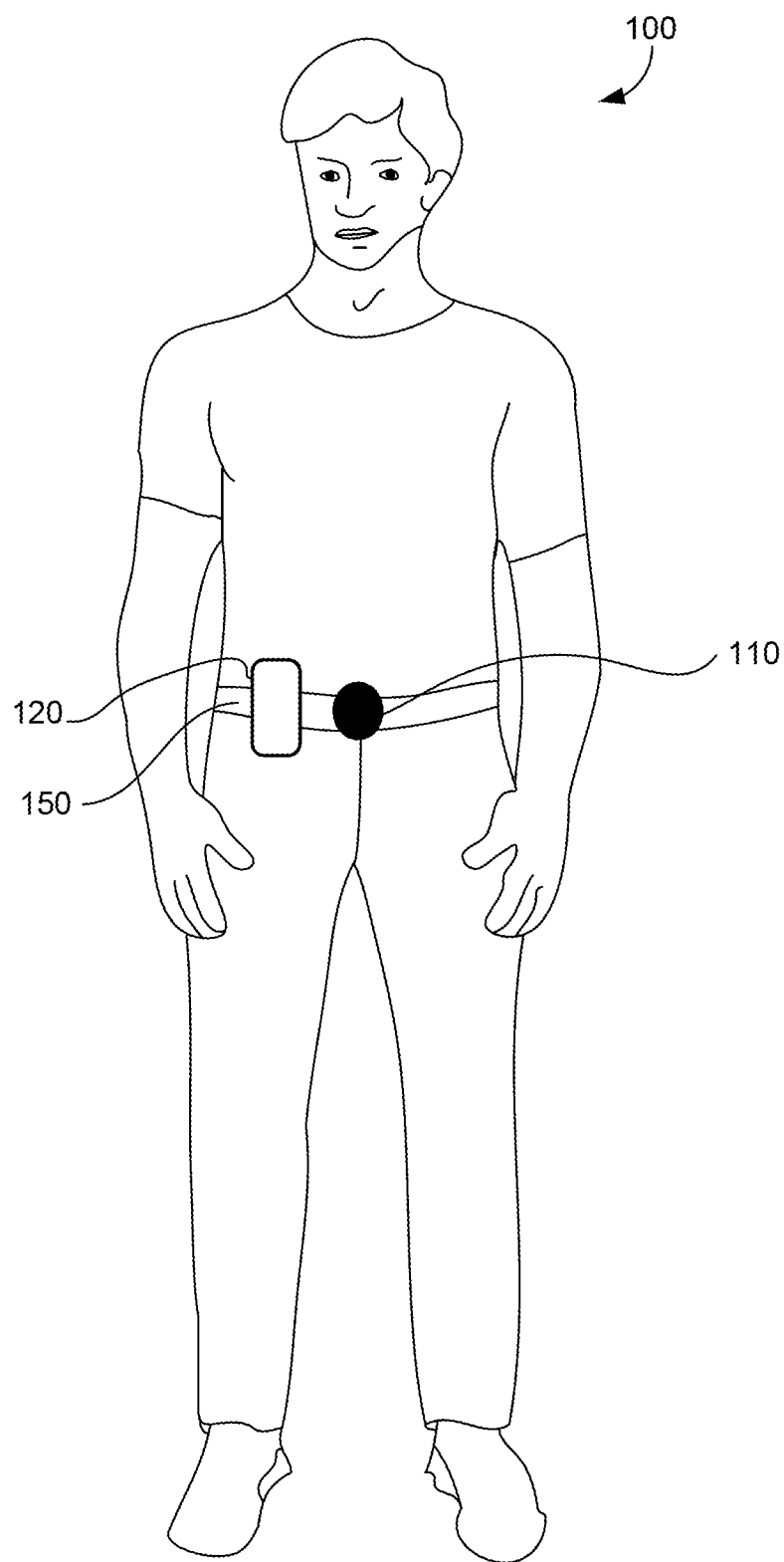
FIG. 1C is a schematic illustration of an example of the user wearing a wearable apparatus according to a disclosed embodiment.

FIG. 1C illustrates user 100 wearing apparatus 110 that is physically connected to a belt 150, consistent with a disclosed embodiment. Such a configuration of apparatus 110 may be designed as a belt buckle. Alternatively, apparatus 110 may include a clip for attaching to various clothing articles, such as bell 150, necklace 140, or a vest, a pocket, a collar, a cap or hat or other portion of a clothing article.

Figure 1D:
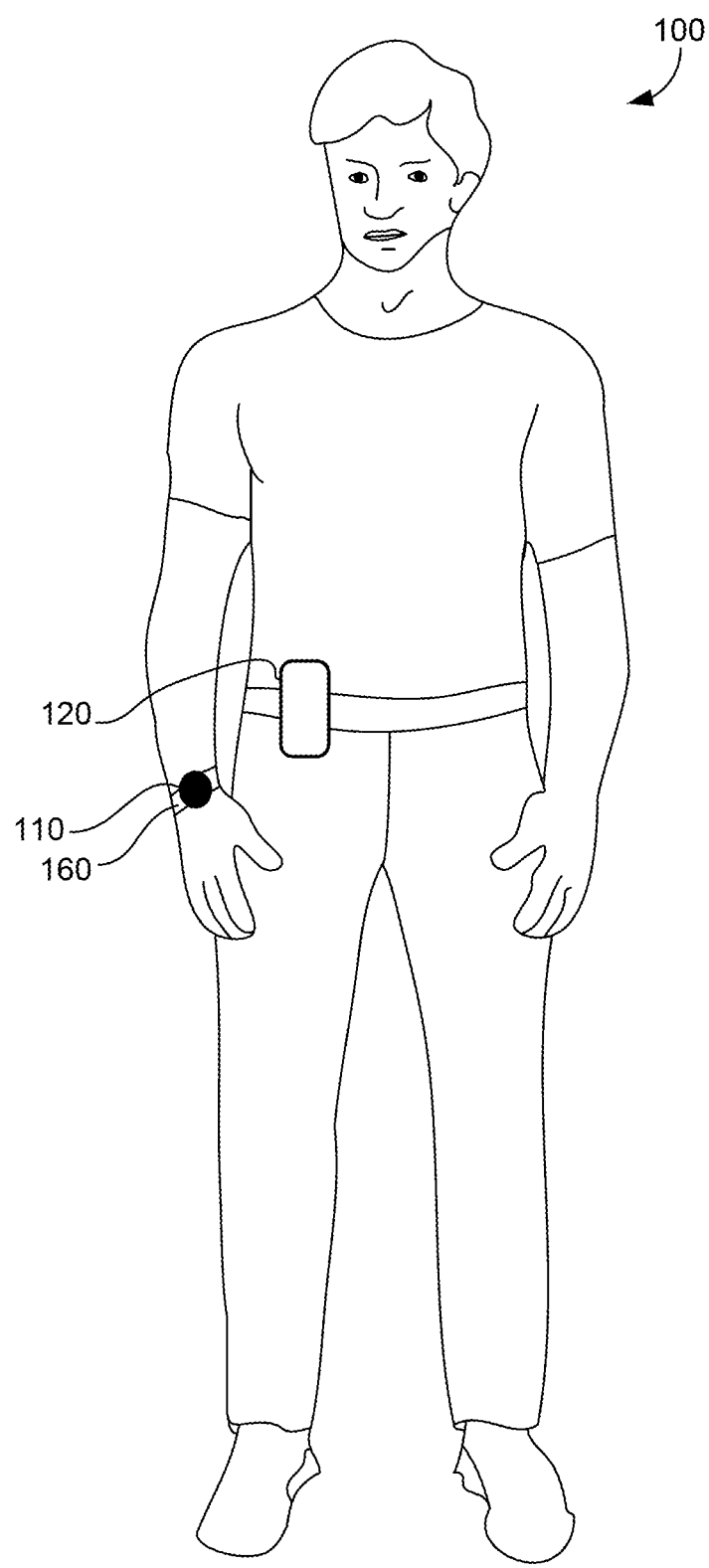
FIG. 1D is a schematic illustration of an example of the user wearing a wearable apparatus according to a disclosed embodiment.

FIG. 1D illustrates user 100 wearing apparatus 110 that is physically connected to a wrist strap 160, consistent with a disclosed embodiment. Although the aiming direction of apparatus 110, according to this embodiment, may not match the field-of-view of user 100, apparatus 110 may include the ability to identify a hand-related trigger based on the tracked eye movement of a user 100 indicating that user 100 is looking in the direction of the wrist strap 160. Wrist strap 160 may also include an accelerometer, a gyroscope, or other sensor for determining movement or orientation of a user's 100 hand for identifying a hand-related trigger.

Figure 2:
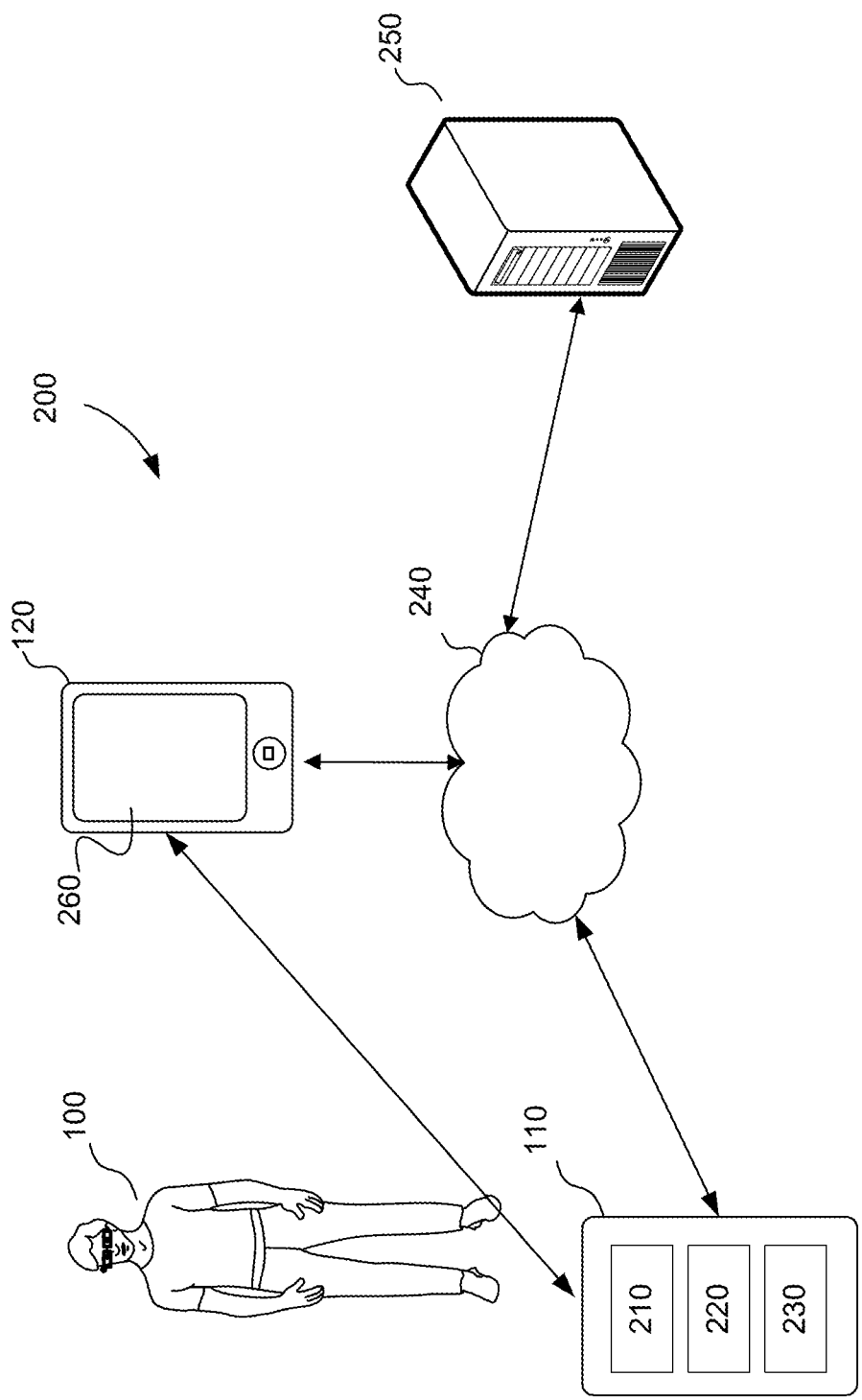
FIG. 2 is a schematic illustration of an example system consistent with the disclosed embodiments.

FIG. 2 is a schematic illustration of an exemplary system 200 including a wearable apparatus 110, worn by user 100, and an optional computing device 120 and/or a server 250 capable of communicating with apparatus 110 via a network 240, consistent with disclosed embodiments. In some embodiments, apparatus 110 may capture and analyze image data, identify a hand-related trigger present in the image data, and perform an action and or provide feedback to a user 100, based at least in part on the identification of the hand-related trigger. In some embodiments, optional computing device 120 and/or server 250 may provide additional functionality to enhance interactions of user 100 with his or her environment, as described in greater detail below.

According to the disclosed embodiments, apparatus 110 may include an image sensor system 220 for capturing real-time image data of the field-of-view of user 100. In some embodiments, apparatus 110 may also include a processor 210 for controlling and performing the disclosed functionality of apparatus 110, such as to control the capture of image data, analyze the image data, and perform an action and/or output a feedback based on a hand-related trigger identified in the image data. According to the disclosed embodiments, a hand-related trigger may include a gesture performed by user 100 involving a portion of a hand of user 100. Further, consistent with some embodiments, a hand-related trigger may include a wrist-related trigger. In some embodiments, the hand-related trigger may include an indicator of consumption, such as the presence of a utensil in a hand, the presence of a consumable product in a hand, motion of the hand to and from the mouth, or other action associated with consumption. Additionally, in some embodiments, apparatus 110 may include a feedback outputting unit 230 for producing an output of information to user 100. Feedback outputting unit 230 may include one or more vibration devices, e.g., a vibration motor, a speaker, or a display.

As discussed above, apparatus 110 may include an image sensor 220 for capturing image data. The term "image sensor" refers to a device capable of detecting and converting optical signals in the near-infrared, infrared, visible, and ultraviolet spectrums into electrical signals. The electrical signals may be used to form an image or a video stream (i.e., image data) based on the detected signal. The term "image data" includes any form of data retrieved from optical signals in the near-infrared, infrared, visible, and ultraviolet spectrums. Examples of image sensors may include semiconductor charge-coupled devices (CCD), active pixel sensors in complementary metal oxide semiconductor (CMOS), or N-type metal-oxide-semiconductor (NMOS, Live MOS). In some cases, image sensor 220 may be part of a camera included in apparatus 110.

Apparatus 110 may also include a processor 210 for controlling image sensor 220 to capture image data and for analyzing the image data according to the disclosed embodiments. As discussed in further detail below with respect to FIG. 5A, processor 210 may include a "processing device" for performing logic operations on one or more inputs of image data and other data according to stored or accessible software instructions providing desired functionality. In some embodiments, processor 210 may also control feedback outputting unit 230 to provide feedback to user 100 including information based on the analyzed image data and the stored software instructions. As the term is used herein, a "processing device" may access memory where executable instructions are stored or, in some embodiments, a "processing device" itself may include executable instructions (e.g., stored in memory included in the processing device).

In some embodiments, the information or feedback information provided to user 100 may include time information. The time information may include any information related to a current time of day and, as described further below, may be presented in any sensory perceptive manner. In some embodiments, time information may include a current time of day in a preconfigured format (e.g., 2:30 pm or 14:30). Time information may include the lime in the user's current time zone (e.g., based on a determined location of user 100), as well as an indication of the time zone and/or a time of day in another desired location. In some embodiments, time information may include a number of hours or minutes relative to one or more predetermined times of day. For example, in some embodiments, time information may include an indication that three hours and fifteen minutes remain until a particular hour (e.g., until 6:00 pm), or some other predetermined time. Time information may also include a duration of time passed since the beginning of a particular activity, such as the start of a meeting or the start of a jog, or any other activity. In some embodiments, the activity may be determined based on analyzed image data. In other embodiments, time information may also include additional information related to a current time and one or more other routine, periodic, or scheduled events. For example, time information may include an indication of the number of minutes remaining until the next scheduled event, as may be determined from a calendar function or other information retrieved from computing device 120 or server 250, as discussed in further detail below.

Feedback outputting unit 230 may include one or more feedback systems for providing the output of information to user 100. In the disclosed embodiments, the audible or visual feedback may be provided via any type of connected audible or visual system or both. Feedback of information according to the disclosed embodiments may include audible feedback to user 100 (e.g., using a Bluetooth® or other wired or wirelessly connected speaker, or a bone conduction headphone). Feedback outputting unit 230 of some embodiments may additionally or alternatively produce a visible output of information to user 100, for example, as part of an augmented reality display projected onto a lens of glasses 130 or provided via a separate heads up display in communication with apparatus 110, such as a display 260 provided as part of computing device 120, which may include an onboard automobile heads up display, an augmented reality device, a virtual reality device, a smartphone, PC, table, etc. In some embodiments, feedback information may include providing vibrational or other tactile feedback to user 100 (e.g., using a vibrating device within or in communication with feedback outputting unit 230).

The term "computing device" refers to a device including a processor or a processing unit and having computing capabilities. Some examples of computing device 120 include a PC, laptop, tablet, or other computing systems such as an on-board computing system of an automobile, for example, each configured to communicate directly with apparatus 110 or server 250 over network 240. Another example of computing device 120 includes a smartphone having a display 260. In some embodiments, computing device 120 may be a computing system configured particularly for apparatus 110, and may be provided integral to apparatus 110 or tethered thereto. Apparatus 110 can also connect to computing device 120 over network 240 via any known wireless standard (e.g., Wi-Fi, Bluetooth®, etc.), as well as near-field capacitive coupling, and other short range wireless techniques, or via a wired connection. In an embodiment in which computing device 120 is a smartphone, computing device 120 may have a dedicated application installed therein. For example, user 100 may view on display 260 data (e.g., images, video clips, extracted information, feedback information, etc.) that originate from or are triggered by apparatus 110. In addition, user 100 may select part of the data for storage in server 250.

Network 240 may be a shared, public, or private network, may encompass a wade area or local area, and may be implemented through any suitable combination of wired and/or wireless communication networks. Network 240 may further comprise an intranet or the Internet. In some embodiments, network 240 may include short range or near-field wireless communication systems for enabling communication between apparatus 110 and computing device 120 provided in close proximity to each other, such as on or near a user's person, for example. Apparatus 110 may establish a connection to network 240 autonomously, for example, using a wireless module (e.g., Wi-Fi, cellular). In some embodiments, apparatus 110 may use the wireless module when being connected to an external power source, to prolong battery life. Further, communication between apparatus 110 and server 250 may be accomplished through any suitable communication channels, such as, for example, a telephone network, an extranet, an intranet, the Internet, satellite communications, off-line communications, wireless communications, transponder communications, a local area network (LAN), a wide area network (WAN), and a virtual private network (VPN).

As shown in FIG. 2, apparatus 110 may transfer or receive data to/from server 250 via network 240. In the disclosed embodiments, the data being received from server 250 and/or computing device 120 may include numerous different types of information based on the analyzed image data, including information related to a commercial product, or a person's identity, an identified landmark, and any other information capable of being stored in or accessed by server 250. In some embodiments, data may be received and transferred via computing device 120. Server 250 and/or computing device 120 may retrieve information from different data sources (e.g., a user specific database or a user's social network account or other account, the Internet, and other managed or accessible databases) and provide information to apparatus 110 related to the analyzed image data and a recognized trigger according to the disclosed embodiments. In some embodiments, calendar-related information retrieved from the different data sources may be analyzed to provide certain time information or a time-based context for providing certain information based on the analyzed image data.

Figure 3A:
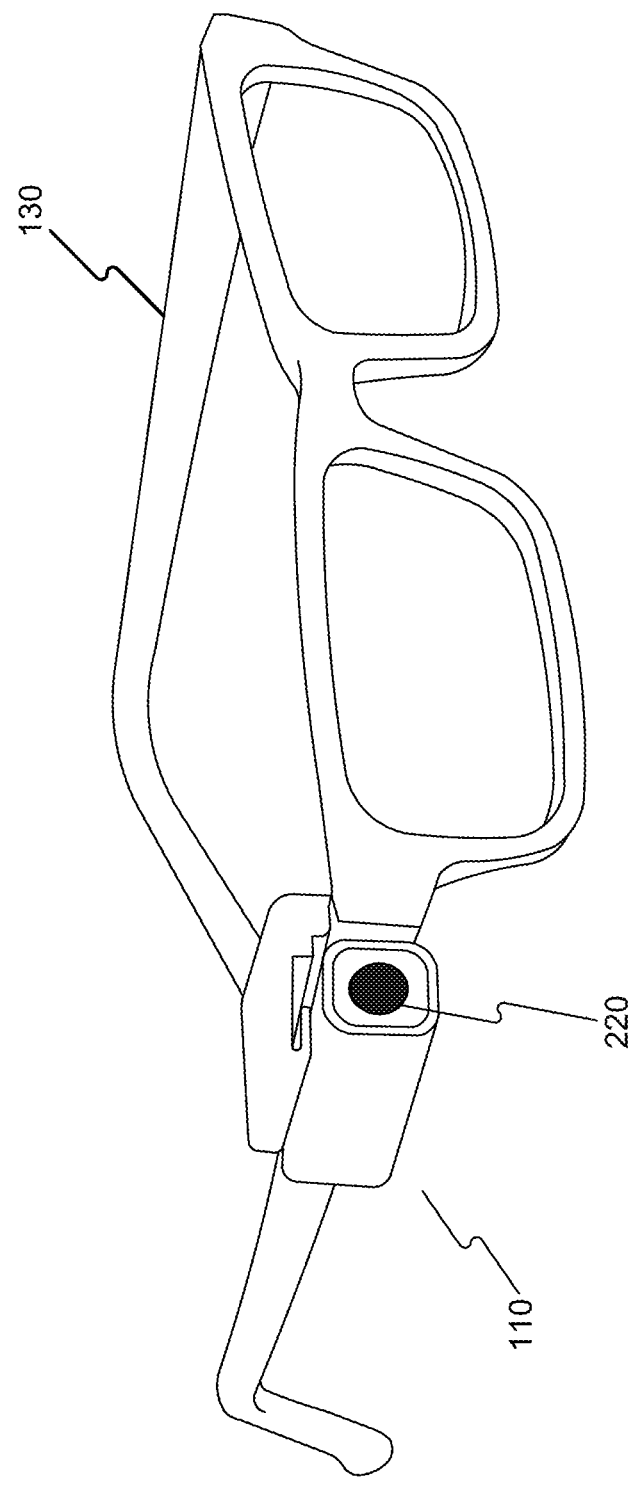
FIG. 3A is a schematic illustration of an example of the wearable apparatus shown in FIG. 1A.

An example of wearable apparatus 110 incorporated with glasses 130 according to some embodiments (as discussed in connection with FIG. 1A) is shown in greater detail in FIG. 3A. In some embodiments, apparatus 110 may be associated with a structure (not shown in FIG. 3A) that enables easy detaching and reattaching of apparatus 110 to glasses 130. In some embodiments, when apparatus 110 attaches to glasses 130, image sensor 220 acquires a set aiming direction without the need for directional calibration. The set aiming direction of image sensor 220 may substantially coincide with the field-of-view of user 100. For example, a camera associated with image sensor 220 may be installed within apparatus 110 in a predetermined angle in a position facing slightly downwards (e.g., 5-15 degrees from the horizon). Accordingly, the set aiming direction of image sensor 220 may substantially match the field-of-view of user 100. In some embodiments, wearable apparatus 110 may include a vibrating device (not shown). The vibrating device may be used to provide feedback to user 100.

Figure 3B:
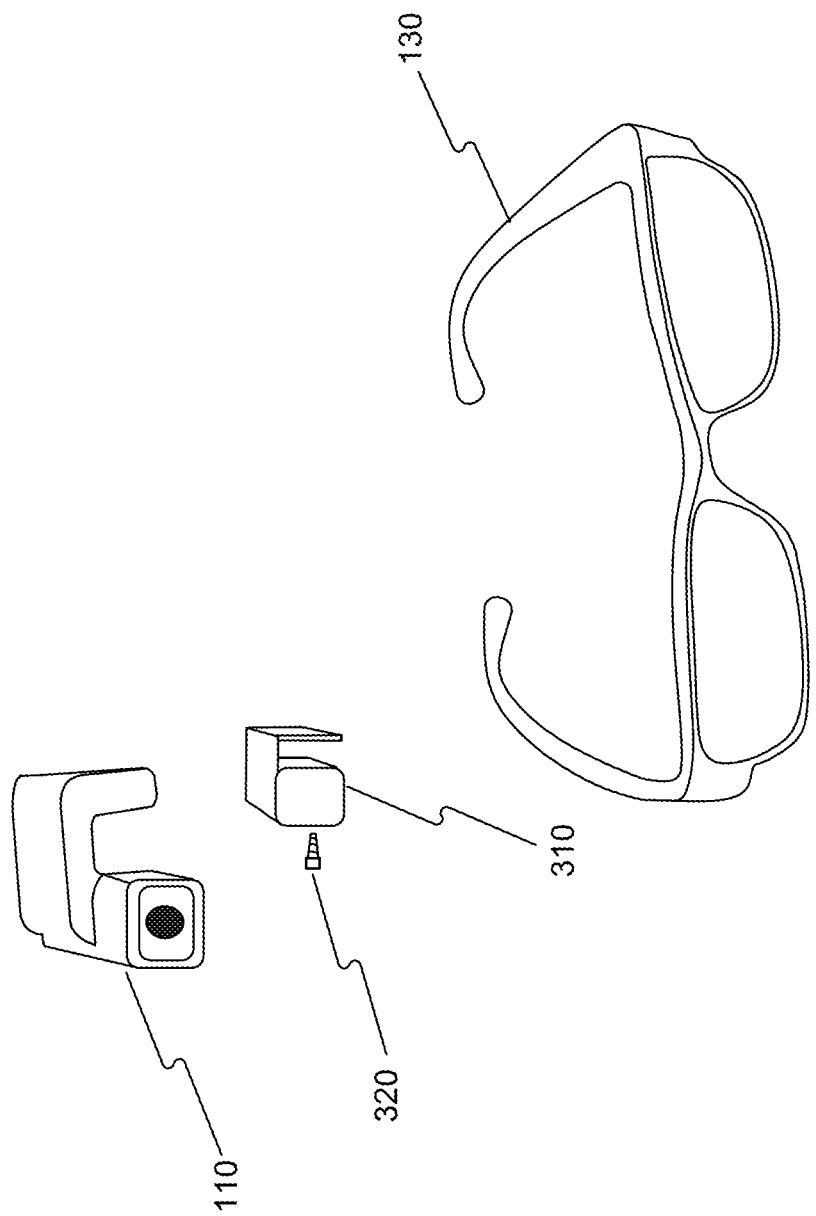
FIG. 3B is an exploded view of the example of the wearable apparatus shown in FIG. 3A.

FIG. 3B is an exploded view of the components of the embodiment discussed regarding FIG. 3A. Attaching apparatus 110 to glasses 130 may take place in the following way. Initially, a support 310 may be mounted on glasses 130 using a screw 320, in the side of support 310. Then, apparatus 110 may be clipped on support 310 such that it is aligned with the field-of-view of user 100. The term "support" includes any device or structure that enables detaching and reattaching of a device including a camera to a pair of glasses or to another object (e.g., a helmet). Support 310 may be made from plastic (e.g., polycarbonate), metal (e.g., aluminum), or a combination of plastic and metal (e.g., carbon fiber graphite). Support 310 may be mounted on any kind of glasses (e.g., eyeglasses, sunglasses, 3D glasses, safety glasses, etc.) using screws, bolts, snaps, or any fastening means used in the art.

In some embodiments, support 310 may include a quick release mechanism for disengaging and reengaging apparatus 110. For example, support 310 and apparatus 110 may include magnetic elements. As an alternative example, support 310 may include a male latch member and apparatus 110 may include a female receptacle. In other embodiments, support 310 can be an integral part of a pair of glasses, or sold separately and installed by an optometrist. For example, support 310 may be configured for mounting on the arms of glasses 130 near the frame front, but before the hinge. Alternatively, support 310 may be configured for mounting on the bridge of glasses 130.

In some embodiments, apparatus 110 may be provided as part of a glasses frame 130, with or without lenses. Additionally, in some embodiments, apparatus 110 may be configured to provide an augmented reality display projected onto a lens of glasses 130 (if provided), or alternatively, may include a display for projecting time information, for example, according to the disclosed embodiments. Apparatus 110 may include the additional display or alternatively, may be in communication with a separately provided display system that may or may not be attached to glasses 130.

Figure 4A:
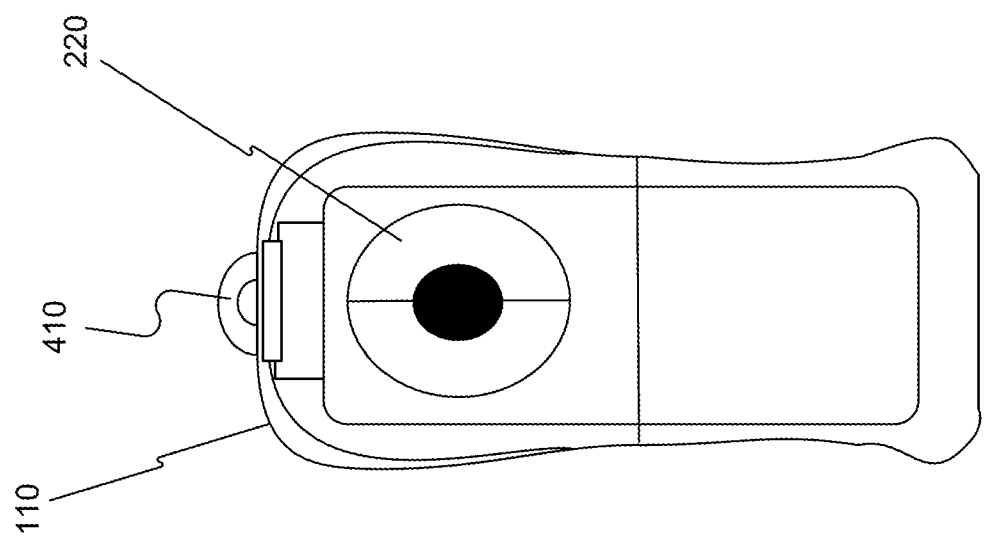
FIG. 4A is a schematic illustration of an example of the wearable apparatus shown in FIG. 1B from a first viewpoint.

In some embodiments, apparatus 110 may be implemented in a form other than wearable glasses, as described above with respect to FIGS. 1B-1D, for example. FIG. 4A is a schematic illustration of an example of an additional embodiment of apparatus 110 from a first viewpoint. The view point shown in FIG. 4A is from the front of apparatus 110. Apparatus 110 includes an image sensor 220, a clip (not shown), a function button (not shown) and a hanging ring 410 for attaching apparatus 110 to, for example, necklace 140, as shown in FIG. 1B. When apparatus 110 hangs on necklace 140, the aiming direction of image sensor 220 may not fully coincide with the field-of-view of user 100, but the aiming direction would still correlate with the field-of-view of user 100.

FIG. 4B is a schematic illustration of the example of a second embodiment of apparatus 110, from a second view point. The viewpoint shown in FIG. 4B is from a side orientation of apparatus 110. In addition to hanging ring 410, as shown in FIG. 4B, apparatus 110 may further include a clip 420. User 100 can use clip 420 to attach apparatus 110 to a shirt or belt 150, as illustrated in FIG. 1C. Clip 420 may provide an easy mechanism for disengaging and reengaging apparatus 110 from different articles of clothing. In other embodiments, apparatus 110 may include a female receptacle for connecting with a male latch of a car mount or universal stand.

In some embodiments, apparatus 110 includes a function button 430 for enabling user 100 to provide input to apparatus 110. Function button 430 may accept different types of tactile input (e.g., a tap, a click, a double-click, a long press, a right-to-left slide, a left-to-right slide). In some embodiments, each type of input may be associated with a different action. For example, a tap may be associated with the function of taking a picture, while a right-to-left slide may be associated with the function of recording a video.

The example embodiments discussed above with respect to FIGS. 3A, 3B, 4A, and 4B are not limiting. In some embodiments, apparatus 110 may be implemented in any suitable configuration for performing the disclosed methods. For example, referring back to FIG. 2, the disclosed embodiments may implement an apparatus 110 according to any configuration including an image sensor 220 and a processor unit 210 to perform image analysis and for communicating with a feedback unit 230.

Figure 5A:
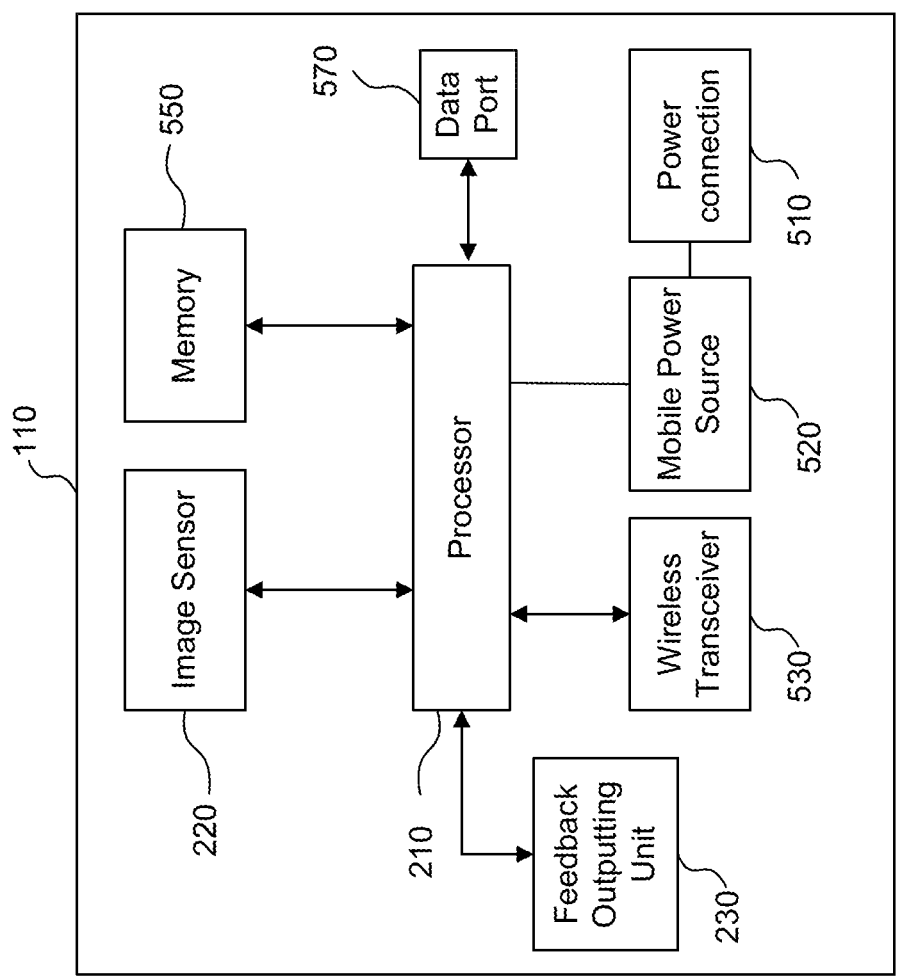
FIG. 5A is a block diagram illustrating an example of the components of a wearable apparatus according to a first embodiment.

FIG. 5A is a block diagram illustrating the components of apparatus 110 according to an example embodiment. As shown in FIG. 5A, and as similarly discussed above, apparatus 110 includes an image sensor 220, a memory 550, a processor 210, a feedback outputting unit 230, a wireless transceiver 530, and a mobile power source 520. In other embodiments, apparatus 110 may also include buttons, other sensors such as a microphone, and inertial measurements devices such as accelerometers, gyroscopes, magnetometers, temperature sensors, color sensors, light sensors, etc. Apparatus 110 may further include a data port 570 and a power connection 510 with suitable interfaces for connecting with an external power source or an external device (not shown).

Processor 210, depicted in FIG. 5A, may include any suitable processing device. The term "processing device" includes any physical device having an electric circuit that performs a logic operation on input or inputs. For example, processing device may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by the processing device may, for example, be pre-loaded into a memory integrated with or embedded into the processing device or may be stored in a separate memory (e.g., memory 550). Memory 550 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although, in the embodiment illustrated in FIG. 5A, apparatus 110 includes one processing device (e.g., processor 210), apparatus 110 may include more than one processing device. Each processing device may have a similar construction, or the processing devices may be of differing constructions that are electrically connected or disconnected from each other. For example, the processing devices may be separate circuits or integrated in a single circuit. When more than one processing device is used, the processing devices may be configured to operate independently or collaboratively. The processing devices may be coupled electrically, magnetically, optically, acoustically, mechanically or by other means that permit them to interact.

In some embodiments, processor 210 may process a plurality of images captured from the environment of user 100 to determine different parameters related to capturing subsequent images. For example, processor 210 can determine, based on information derived from captured image data, a value for at least one of the following: an image resolution, a compression ratio, a cropping parameter, frame rate, a focus point, an exposure time, an aperture size, and a light sensitivity. The determined value may be used in capturing at least one subsequent image. Additionally, processor 210 can detect images including at least one hand-related trigger in the environment of the user and perform an action and or provide an output of information to a user via feedback outputting unit 230.

In another embodiment, processor 210 can change the aiming direction of image sensor 220. For example, when apparatus 110 is attached with clip 420, the aiming direction of image sensor 220 may not coincide with the field-of-view of user 100. Processor 210 may recognize certain situations from the analyzed image data and adjust the aiming direction of image sensor 220 to capture relevant image data. For example, in one embodiment, processor 210 may detect an interaction with another individual and sense that the individual is not fully in view, because image sensor 220 is tilted down. Responsive thereto, processor 210 may adjust the aiming direction of image sensor 220 to capture image data of the individual. Other scenarios are also contemplated where processor 210 may recognize the need to adjust an aiming direction of image sensor 220.

In some embodiments, processor 210 may communicate data to feedback outputting unit 230, which may include any device configured to provide information to a user 100. Feedback outputting unit 230 may be provided as part of apparatus 110 (as shown) or may be provided external to apparatus 110 and communicatively coupled thereto. Feedback-outputting unit 230 may be configured to output visual or nonvisual feedback based on signals received from processor 210, such as when processor 210 recognizes a hand-related trigger in the analyzed image data.

The term "feedback" refers to any output or information provided in response to processing at least one image in an environment. In some embodiments, as similarly described above, feedback may include an audible or visible indication of time information, detected text or numerals, the value of currency, a branded product, a person's identity, the identity of a landmark or other environmental situation or condition including the street names at an intersection or the color of a traffic light, etc., as well as other information associated with each of these. For example, in some embodiments, feedback may include additional information regarding the amount of currency still needed to complete a transaction, information regarding the identified person, historical information or times and prices of admission, etc. of a detected landmark, etc. In some embodiments, feedback may include an audible tone, a tactile response, and/or information previously recorded by user 100. Feedback-outputting unit 230 may comprise appropriate components for outputting acoustical and tactile feedback. For example, feedback-outputting unit 230 may comprise audio headphones, a vibrating device, a hearing aid type device, a speaker, a bone conduction headphone, interfaces that provide tactile cues, vibrotactile stimulators, etc. In some embodiments, processor 210 may communicate signals with an external feedback outputting unit 230 via a wireless transceiver 530, a wired connection, or some other communication interface. In some embodiments, feedback outputting unit 230 may also include any suitable display device for visually displaying information to user 100.

As shown in FIG. 5A, apparatus 110 includes memory 550. Memory 550 may include one or more sets of instructions accessible to processor 210 to perform the disclosed methods, including instructions for recognizing a hand-related trigger in the image data. In some embodiments memory 550 may store image data (e.g., images, videos) captured from the environment of user 100. In addition, memory 550 may store information specific to user 100, such as image representations of known individuals, favorite products, personal items, and calendar or appointment information, etc. In some embodiments, processor 210 may determine, for example, which type of image data to store based on available storage space in memory 550. In another embodiment, processor 210 may extract information from the image data stored in memory 550.

As further shown in FIG. 5A, apparatus 110 includes mobile power source 520. The term "mobile power source" includes any device capable of providing electrical power, which can be easily carried by hand (e.g., mobile power source 520 may weigh less than a pound). The mobility of the power source enables user 100 to use apparatus 110 in a variety of situations. In some embodiments, mobile power source 520 may include one or more batteries (e.g., nickel-cadmium batteries, nickel-metal hydride batteries, and lithium-ion batteries) or any other type of electrical power supply. In other embodiments, mobile power source 520 may be rechargeable and contained within a casing that holds apparatus 110. In yet other embodiments, mobile power source 520 may include one or more energy harvesting devices for converting ambient energy into electrical energy (e.g., portable solar power units, human vibration units, etc.).

Mobile power source 520 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data, processed image data, extracted information) from apparatus 110 to computing device 120 and/or server 250. Wireless transceiver 530 may also receive data from computing device 120 and/or server 250. In other embodiments, wireless transceiver 530 may transmit data and instructions to an external feedback outputting unit 230.

Figure 5B:
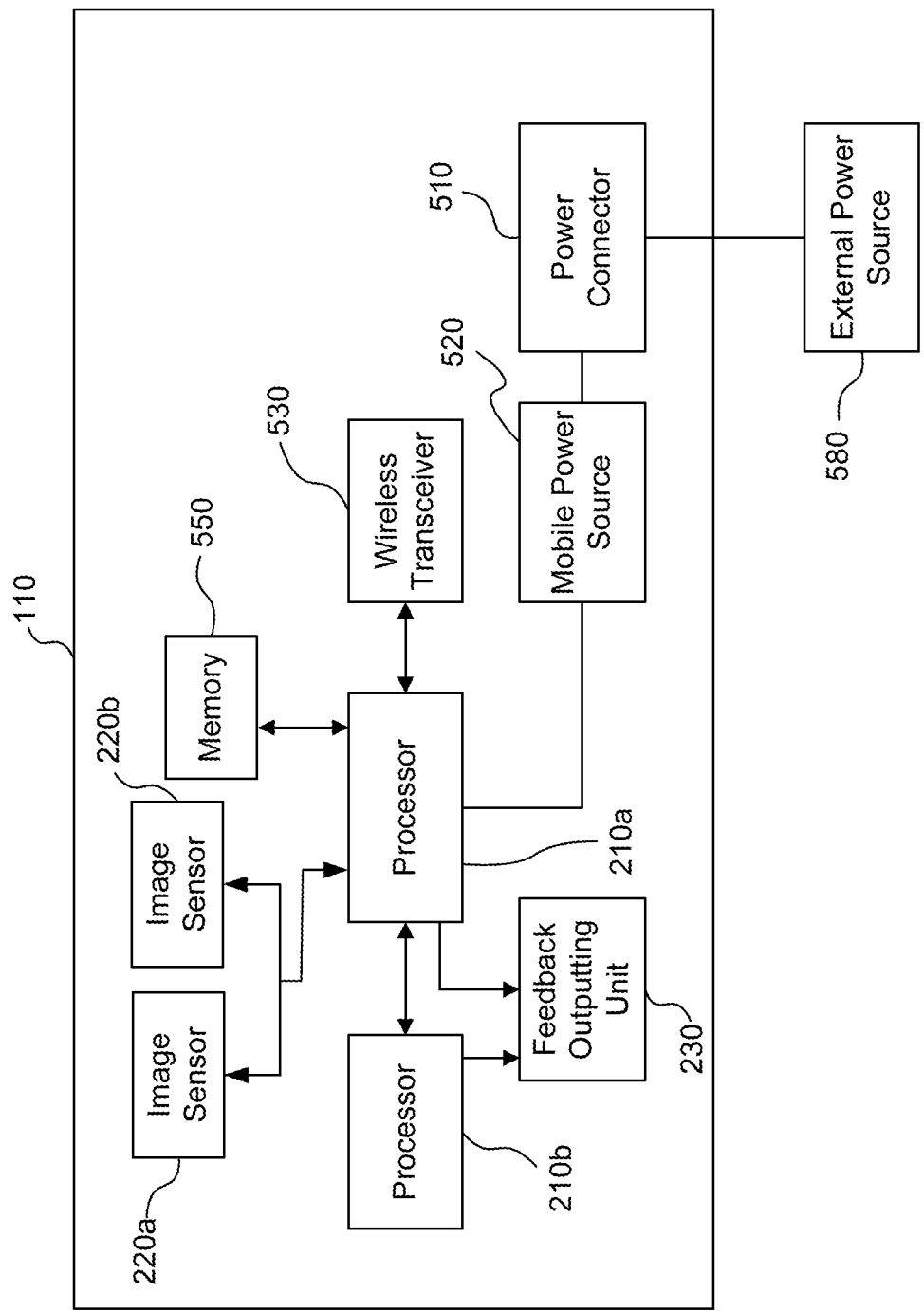
FIG. 5B is a block diagram illustrating an example of the components of a wearable apparatus according to a second embodiment.

FIG. 5B is a block diagram illustrating the components of apparatus 110 according to another example embodiment. In some embodiments, apparatus 110 includes a first image sensor 220a, a second image sensor 220b, a memory 550, a first processor 210a, a second processor 210b, a feedback outputting unit 230, a wireless transceiver 530, a mobile power source 520, and a power connector 510. In the arrangement shown in FIG. 5B, each of the image sensors may provide images in a different image resolution, or face a different direction. Alternatively, each image sensor may be associated with a different camera (e.g., a wide angle camera, a narrow angle camera, an IR camera, etc.). In some embodiments, apparatus 110 can select which image sensor to use based on various factors. For example, processor 210a may determine, based on available storage space in memory 550, to capture subsequent images in a certain resolution.

Apparatus 110 may operate in a first processing-mode and in a second processing-mode, such that the first processing-mode may consume less power than the second processing-mode. For example, in the first processing-mode, apparatus 110 may capture images and process the captured images to make real-time decisions based on an identifying hand-related trigger, for example. In the second processing-mode, apparatus 110 may extract information from stored images in memory 550 and delete images from memory 550. In some embodiments, mobile power source 520 may provide more than fifteen hours of processing in the first processing-mode and about three hours of processing in the second processing-mode. Accordingly, different processing-modes may allow mobile power source 520 to produce sufficient power for powering apparatus 110 for various time periods (e.g., more than two hours, more than four hours, more than ten hours, etc.).

In some embodiments, apparatus 110 may use first processor 210a in the first processing-mode when powered by mobile power source 520, and second processor 210b in the second processing-mode when powered by external power source 580 that is connectable via power connector 510. In other embodiments, apparatus 110 may determine, based on predefined conditions, which processors or which processing modes to use. Apparatus 110 may operate in the second processing-mode even when apparatus 110 is not powered by external power source 580. For example, apparatus 110 may determine that it should operate in the second processing-mode when apparatus 110 is not powered by external power source 580, if the available storage space in memory 550 for storing new image data is lower than a predefined threshold.

Although one wireless transceiver is depicted in FIG. 5B, apparatus 110 may include more than one wireless transceiver (e.g., two wireless transceivers). In an arrangement with more than one wireless transceiver, each of the wireless transceivers may use a different standard to transmit and/or receive data. In some embodiments, a first wireless transceiver may communicate with server 250 or computing device 120 using a cellular standard (e.g., LTE or GSM), and a second wireless transceiver may communicate with server 250 or computing device 120 using a short-range standard (e.g., Wi-Fi or Bluetooth®). In some embodiments, apparatus 110 may use the first wireless transceiver when the wearable apparatus is powered by a mobile power source included in the wearable apparatus, and use the second wireless transceiver when the wearable apparatus is powered by an external power source.

Figure 5C:
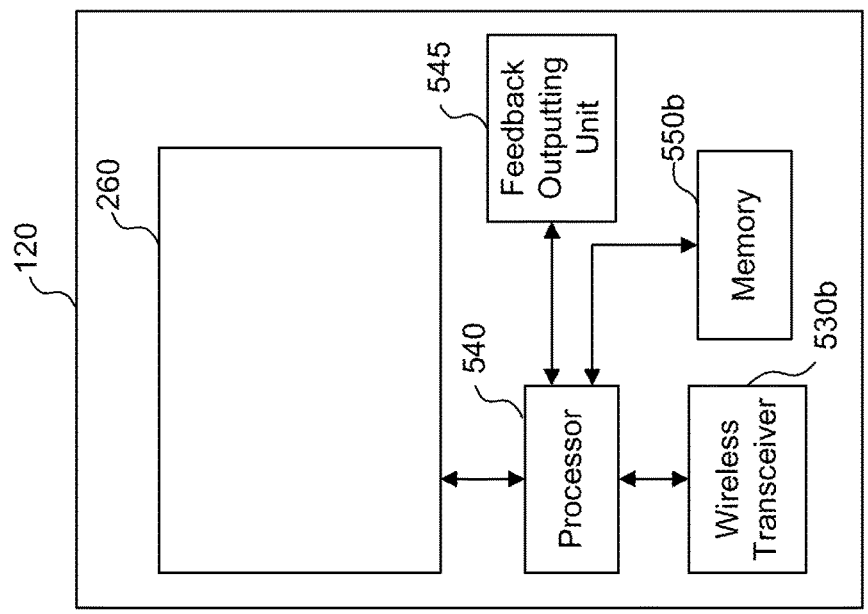
FIG. 5C is a block diagram illustrating an example of the components of a wearable apparatus according to a third embodiment.
Figure 5C:
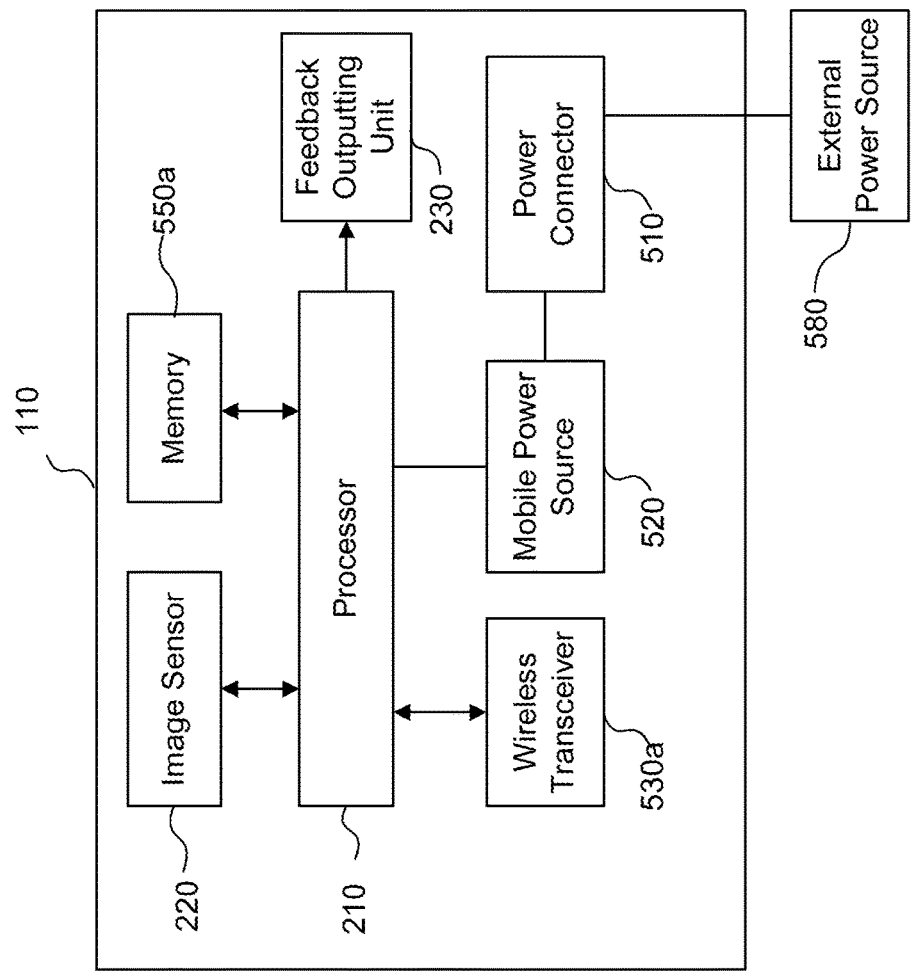

FIG. 5C is a block diagram illustrating the components of apparatus 110 according to another example embodiment including computing device 120. In this embodiment, apparatus 110 includes an image sensor 220, a memory 550a, a first processor 210, a feedback-outputting unit 230, a wireless transceiver 530a, a mobile power source 520, and a power connector 510. As further shown in FIG. 5C, computing device 120 includes a processor 540, a feedback-outputting unit 545, a memory 550b, a wireless transceiver 530b, and a display 260. One example of computing device 120 is a smartphone or tablet having a dedicated application installed therein. In other embodiments, computing device 120 may include any configuration such as an on-board automobile computing system, a PC, a laptop, and any other system consistent with the disclosed embodiments. In this example, user 100 may view feedback output in response to identification of a hand-related trigger on display 260. Additionally, user 100 may view other data (e.g., images, video clips, object information, schedule information, extracted information, etc.) on display 260. In addition, user 100 may communicate with server 250 via computing device 120.

In some embodiments, processor 210 and processor 540 are configured to extract information from captured image data. The term "extracting information" includes any process by which information associated with objects, individuals, locations, events, etc., is identified in the captured image data by any means known to those of ordinary skill in the art.

In some embodiments, apparatus 110 may use the extracted information to send feedback or other real-time indications to feedback outputting unit 230 or to computing device 120. In some embodiments, processor 210 may identify in the image data the individual standing in front of user 100, and send computing device 120 the name of the individual and the last time user 100 met the individual. In another embodiment, processor 210 may identify in the image data, one or more visible triggers, including a hand-related trigger, and determine whether the trigger is associated with a person other than the user of the wearable apparatus to selectively determine whether to perform an action associated with the trigger. One such action may be to provide a feedback to user 100 via feedback-outputting unit 230 provided as part of (or in communication with) apparatus 110 or via a feedback unit 545 provided as part of computing device 120. For example, feedback-outputting unit 545 may be in communication with display 260 to cause the display 260 to visibly output information. In some embodiments, processor 210 may identify in the image data a hand-related trigger and send computing device 120 an indication of the trigger. Processor 540 may then process the received trigger information and provide an output via feedback outputting unit 545 or display 260 based on the hand-related trigger. In other embodiments, processor 540 may determine a hand-related trigger and provide suitable feedback similar to the above, based on image data received from apparatus 110. In some embodiments, processor 540 may provide instructions or other information, such as environmental information to apparatus 110 based on an identified hand-related trigger.

In some embodiments, processor 210 may identify other environmental information in the analyzed images, such as an individual standing in front user 100, and send computing device 120 information related to the analyzed information such as the name of the individual and the last time user 100 met the individual. In a different embodiment, processor 540 may extract statistical information from captured image data and forward the statistical information to server 250. For example, certain information regarding the types of items a user purchases, or the frequency a user patronizes a particular merchant, etc. may be determined by processor 540. Based on this information, server 250 may send computing device 120 coupons and discounts associated with the user's preferences.

When apparatus 110 is connected or wirelessly connected to computing device 120, apparatus 110 may transmit at least part of the image data stored in memory 550a for storage in memory 550b. In some embodiments, after computing device 120 confirms that transferring the part of image data was successful, processor 540 may delete the part of the image data. The term "delete" means that the image is marked as 'deleted' and other image data may be stored instead of it, but docs not necessarily mean that the image data was physically removed from the memory.

As will be appreciated by a person skilled in the art having the benefit of this disclosure, numerous variations and/or modifications may be made to the disclosed embodiments. Not all components are essential for the operation of apparatus 110. Any component may be located in any appropriate apparatus and the components may be rearranged into a variety of configurations while providing the functionality of the disclosed embodiments. For example, in some embodiments, apparatus 110 may include a camera, a processor, and a wireless transceiver for sending data to another device. Therefore, the foregoing configurations are examples and, regardless of the configurations discussed above, apparatus 110 can capture, store, and or process images.

Further, the foregoing and following description refers to storing and/or processing images or image data. In the embodiments disclosed herein, the stored and or processed images or image data may comprise a representation of one or more images captured by image sensor 220. As the term is used herein, a "representation" of an image (or image data) may include an entire image or a portion of an image. A representation of an image (or image data) may have the same resolution or a lower resolution as the image (or image data), andor a representation of an image (or image data) may be altered in some respect (e.g., be compressed, have a lower resolution, have one or more colors that are altered, etc.).

For example, apparatus 110 may capture an image and store a representation of the image that is compressed as a JPG file. As another example, apparatus 110 may capture an image in color, but store a black-and-white representation of the color image. As yet another example, apparatus 110 may capture an image and store a different representation of the image (e.g., a portion of the image). For example, apparatus 110 may store a portion of an image that includes a face of a person who appears in the image, but that does not substantially include the environment surrounding the person. Similarly, apparatus 110 may, for example, store a portion of an image that includes a product that appears in the image, but does not substantially include the environment surrounding the product. As yet another example, apparatus 110 may store a representation of an image at a reduced resolution (i.e., at a resolution that is of a lower value than that of the captured image). Storing representations of images may allow apparatus 110 to save storage space in memory 550. Furthermore, processing representations of images may allow apparatus 110 to improve processing efficiency and or help to preserve battery life.

In addition to the above, in some embodiments, any one of apparatus 110 or computing device 120, via processor 210 or 540, may further process the captured image data to provide additional functionality to recognize objects andor gestures and/or other information in the captured image data. In some embodiments, actions may be taken based on the identified objects, gestures, or other information. In some embodiments, processor 210 or 540 may identity in the image data, one or more visible triggers, including a hand-related trigger, and determine whether the trigger is associated with a person other than the user to determine whether to perform an action associated with the trigger.

Some embodiments of the present disclosure may include an apparatus securable to an article of clothing, of a user. Such an apparatus may include two portions, connectable by a connector. A capturing unit may be designed to be worn on the outside of a user's clothing, and may include an image sensor for capturing images of a user's environment. The capturing unit may be connected to or connectable to a power unit, which may be configured to house a power source and a processing device. The capturing unit may be a small device including a camera or other device for capturing images. The capturing unit may be designed to be inconspicuous and unobtrusive, and may be configured to communicate with a power unit concealed by a user's clothing. The power unit may include bulkier aspects of the system, such as transceiver antennas, at least one battery, a processing device, etc. In some embodiments, communication between the capturing unit and the power unit may be provided by a data cable included in the connector, while in other embodiments, communication may be wirelessly achieved between the capturing unit and the power unit.

Some embodiments may permit alteration of the orientation of an image sensor of the capture unit, for example to better capture images of interest.

An apparatus consistent with embodiments of the present disclosure may also include at least one vibrating device. For example, the vibrating device may be integrated with the wearable apparatus and/or may be housed in a unit separate from and in communication with the wearable apparatus (e.g., a smartphone, a smartwatch, a tablet, or the like).

Figure 6:
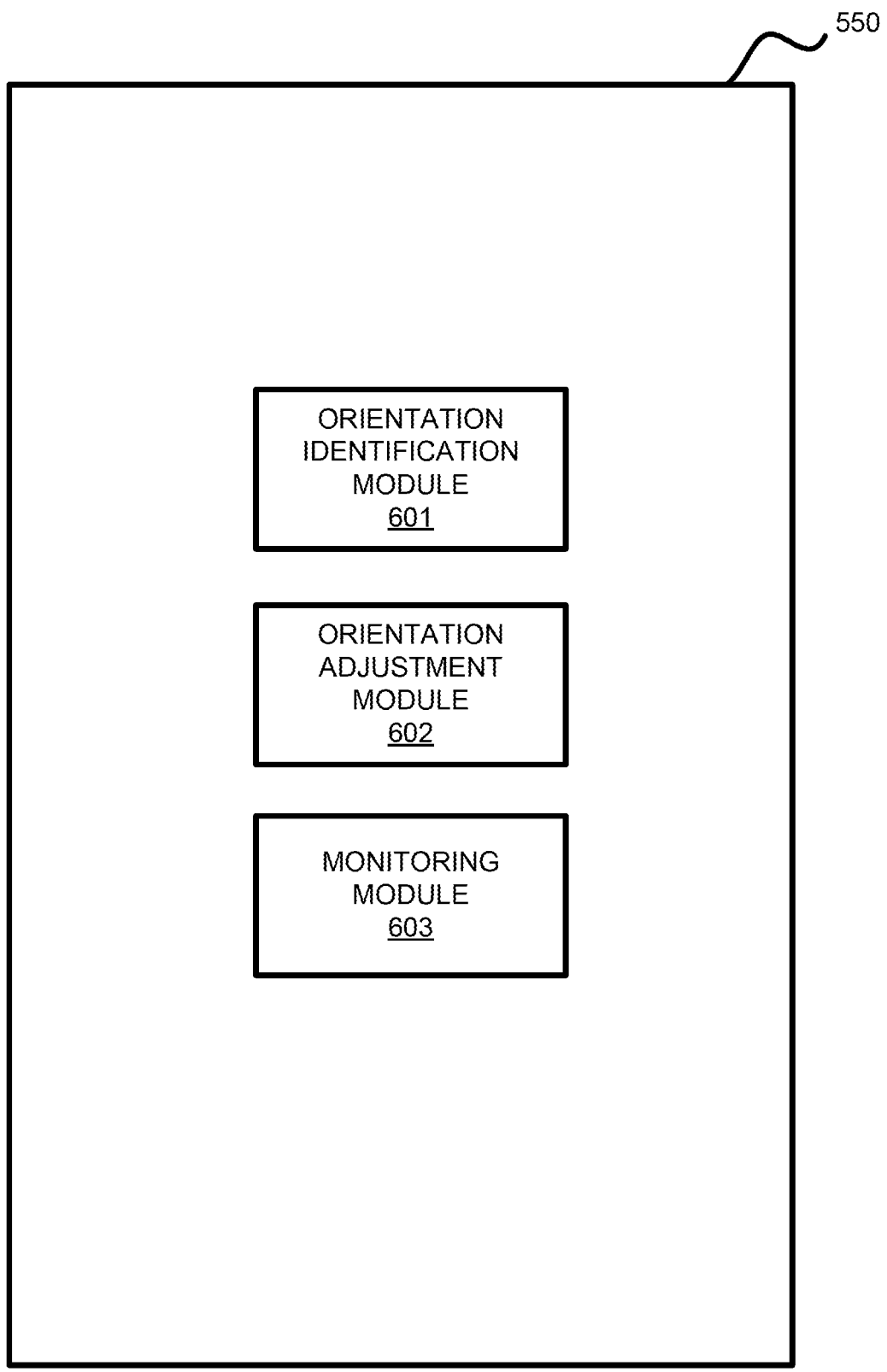
FIG. 6 illustrates an exemplary embodiment of a memory containing software modules consistent with the present disclosure.

FIG. 6 illustrates an exemplary embodiment of a memory containing software modules consistent with the present disclosure. Included in memory 550 are orientation identification module 601, orientation adjustment module 602, and motion tracking module 603. Modules 601, 602, 603 may contain software instructions for execution by at least one processing device, e.g., processor 210, included with a wearable apparatus. Orientation identification module 601, orientation adjustment module 602, and motion tracking module 603 may cooperate to provide orientation adjustment for a capturing unit incorporated into wireless apparatus 110.

Figure 7:
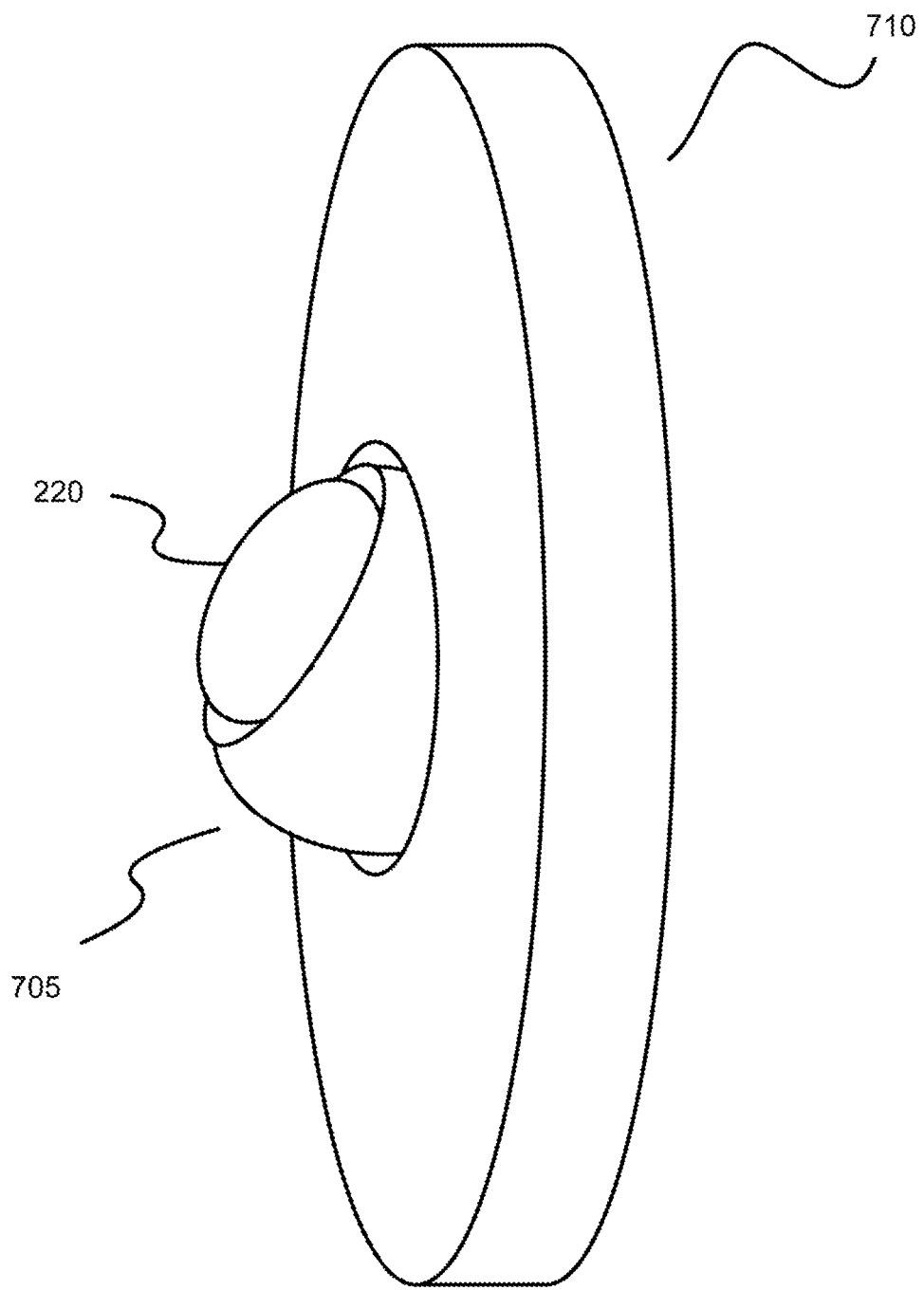
FIG. 7 is a schematic illustration of an embodiment of a wearable apparatus including an orientable image capture unit.

FIG. 7 illustrates an exemplary capturing unit 710 including an orientation adjustment unit 705. Orientation adjustment unit 705 may be configured to permit the adjustment of image sensor 220. As illustrated in FIG. 7, orientation adjustment unit 705 may include an eye-ball type adjustment mechanism. In alternative embodiments, orientation adjustment unit 705 may include gimbals, adjustable stalks, pivotable mounts, and any other suitable unit for adjusting an orientation of image sensor 220.

Image sensor 220 may be configured to be movable with the head of user 100 in such a manner that an aiming direction of image sensor 220 substantially coincides with a field of view of user 100. For example, as described above, a camera associated with image sensor 220 may be installed within capturing unit 710 at a predetermined angle in a position facing slightly upwards or downwards, depending on an intended location of capturing unit 710. Accordingly, the set aiming direction of image sensor 220 may match the field-of-view of user 100. In some embodiments, processor 210 may change the orientation of image sensor 220 using image data provided from image sensor 220. For example, processor 210 may recognize that a user is reading a book and determine that the aiming direction of image sensor 220 is offset from the text. That is, because the words in the beginning of each line of text are not fully in view, processor 210 may determine that image sensor 220 is tilted in the wrong direction. Responsive thereto, processor 210 may adjust the aiming direction of image sensor 220.

Orientation identification module 601 may be configured to identify an orientation of an image sensor 220 of capturing unit 710. An orientation of an image sensor 220 may be identified, for example, by analysis of images captured by image sensor 220 of capturing unit 710, by tilt or attitude sensing devices within capturing unit 710, and by measuring a relative direction of orientation adjustment unit 705 with respect to the remainder of capturing unit 710.

Orientation adjustment module 602 may be configured to adjust an orientation of image sensor 220 of capturing unit 710. As discussed above, image sensor 220 may be mounted on an orientation adjustment unit 705 configured for movement. Orientation adjustment unit 705 may be configured for rotational and/or lateral movement in response to commands from orientation adjustment module 602. In some embodiments orientation adjustment unit 705 may be adjust an orientation of image sensor 220 via motors, electromagnets, permanent magnets, and/or any suitable combination thereof.

In some embodiments, monitoring module 603 may be provided for continuous monitoring. Such continuous monitoring may include tracking a movement of at least a portion, an object included in one or more images captured by the image sensor. For example, in one embodiment, apparatus 110 may track an object as long as the object remains substantially within the field-of-view of image sensor 220. In additional embodiments, monitoring module 603 may engage orientation adjustment module 602 to instruct orientation adjustment unit 705 to continually orient image sensor 220 towards an object of interest. For example, in one embodiment, monitoring module 603 may cause image sensor 220 to adjust an orientation to ensure that a certain designated object, for example, the face of a particular person, remains within the field-of view of image sensor 220, even as that designated object moves about. In another embodiment, monitoring module 603 may continuously monitor an area of interest included in one or more images captured by the image sensor. For example, a user may be occupied by a certain task, for example, typing on a laptop, while image sensor 220 remains oriented in a particular direction and continuously monitors a portion of each image from a series of images to detect a trigger or other event. For example, image sensor 210 may be oriented towards a piece of laboratory equipment and monitoring module 603 may be configured to monitor a status light on the laboratory equipment for a change in status, while the user's attention is otherwise occupied.

In some embodiments consistent with the present disclosure, capturing unit 710 may include a plurality of image sensors 220. The plurality of image sensors 220 may each be configured to capture different image data. For example, when a plurality of image sensors 220 are provided, the image sensors 220 may capture images having different resolutions, may capture wider or narrower fields of view, and may have different levels of magnification. Image sensors 220 may be provided with varying lenses to permit these different configurations. In some embodiments, a plurality of image sensors 220 may include image sensors 220 having different orientations. Thus, each of the plurality of image sensors 220 may be pointed in a different direction to capture different images. The fields of view of image sensors 220 may be overlapping in some embodiments. The plurality of image sensors 220 may each be configured for orientation adjustment, for example, by being paired with an image adjustment unit 705. In some embodiments, monitoring module 603, or another module associated with memory 550, may be configured to individually adjust the orientations of the plurality of image sensors 220 as well as to turn each of the plurality of image sensors 220 on or off as may be required. In some embodiments, monitoring an object or person captured by an image sensor 220 may include tracking movement of the object across the fields of view of the plurality of image sensors 220.

Embodiments consistent with the present disclosure may include connectors configured to connect a capturing unit and a power unit of a wearable apparatus. Capturing units consistent with the present disclosure may include at least one image sensor configured to capture images of an environment of a user. Power units consistent with the present disclosure may be configured to house a power source and/or at least one processing device. Connectors consistent with the present disclosure may be configured to connect the capturing unit and the power unit, and may be configured to secure the apparatus to an article of clothing such that the capturing unit is positioned over an outer surface of the article of clothing and the power unit is positioned under an inner surface of the article of clothing. Exemplary embodiments of capturing units, connectors, and power units consistent with the disclosure are discussed in further detail with respect to FIGS. 8-14.

Figure 8:
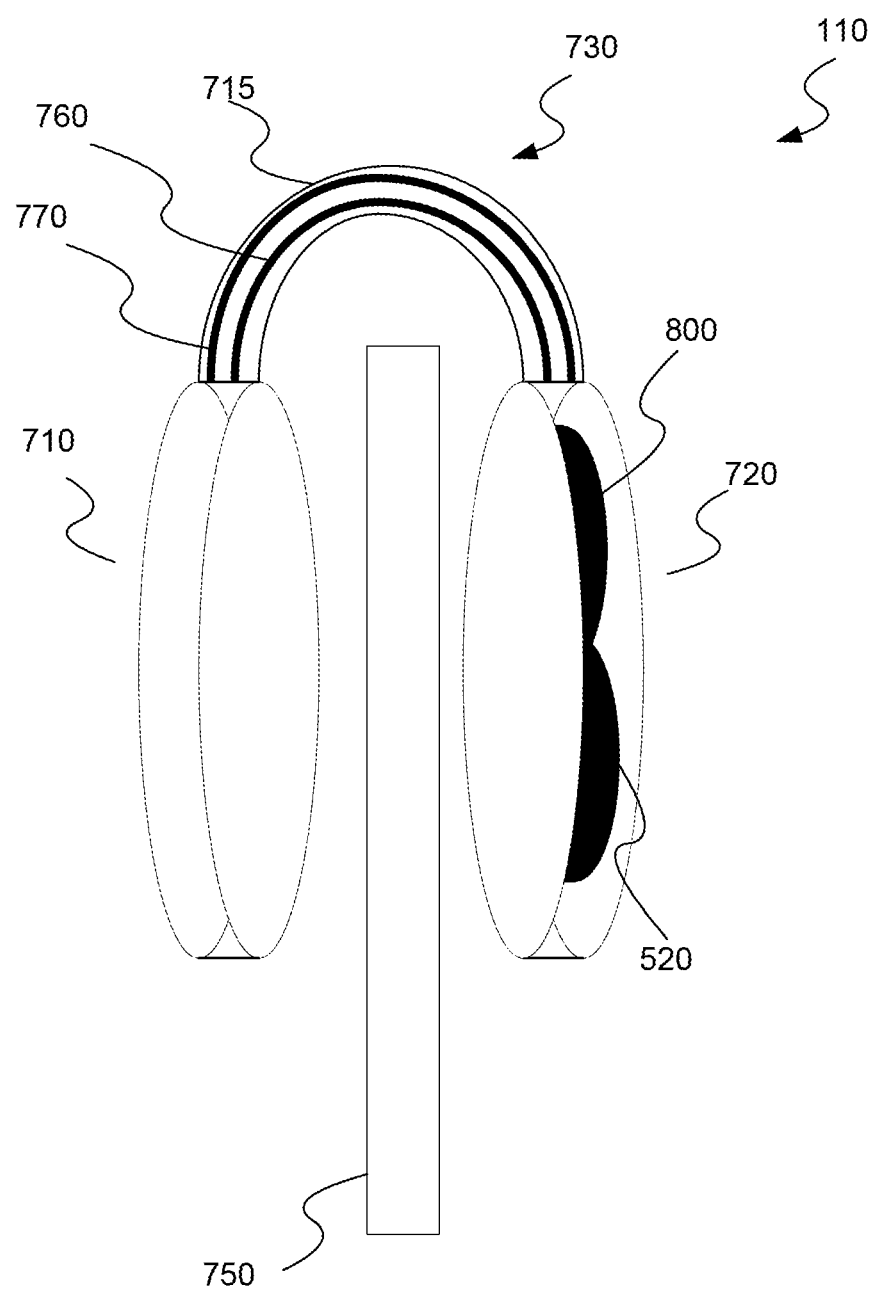
FIG. 8 is a schematic illustration of an embodiment of a wearable apparatus securable to an article of clothing consistent with the present disclosure.

FIG. 8 is a schematic illustration of an embodiment of wearable apparatus 110 securable to an article of clothing consistent with the present disclosure. As illustrated in FIG. 8, capturing unit 710 and power unit 720 may be connected by a connector 730 such that capturing unit 710 is positioned on one side of an article of clothing 750 and power unit 720 is positioned on the opposite side of the clothing 750. In some embodiments, capturing unit 710 may be positioned over an outer surface of the article of clothing 750 and power unit 720 may be located under an inner surface of the article of clothing 750. The power unit 720 may be configured to be placed against the skin of a user.

Capturing unit 710 may include an image sensor 220 and an orientation adjustment unit 705 (as illustrated in FIG. 7). Power unit 720 may include mobile power source 520 and processor 210. Power unit 720 may further include any combination of elements previously discussed that may be a part of wearable apparatus 110, including, but not limited to, wireless transceiver 530, feedback outputting unit 230, memory 550, and data port 570.

Connector 730 may include a clip 715 or other mechanical connection designed to clip or attach capturing unit 710 and power unit 720 to an article of clothing 750 as illustrated in FIG. 8. As illustrated, clip 715 may connect to each of capturing unit 710 and power unit 720 at a perimeter thereof, and may wrap around an edge of the article of clothing 750 to affix the capturing unit 710 and power unit 720 in place. Connector 730 may further include a power cable 760 and a data cable 770. Power cable 760 may be capable of conveying power from mobile power source 520 to image sensor 220 of capturing unit 710. Power cable 760 may also be configured to provide power to any other elements of capturing unit 710, e.g., orientation adjustment unit 705. Data cable 770 may be capable of conveying captured image data from image sensor 220 in capturing unit 710 to processor 800 in the power unit 720. Data cable 770 may be further capable of conveying additional data between capturing unit 710 and processor 800, e.g., control instructions for orientation adjustment unit 705.

Figure 9:
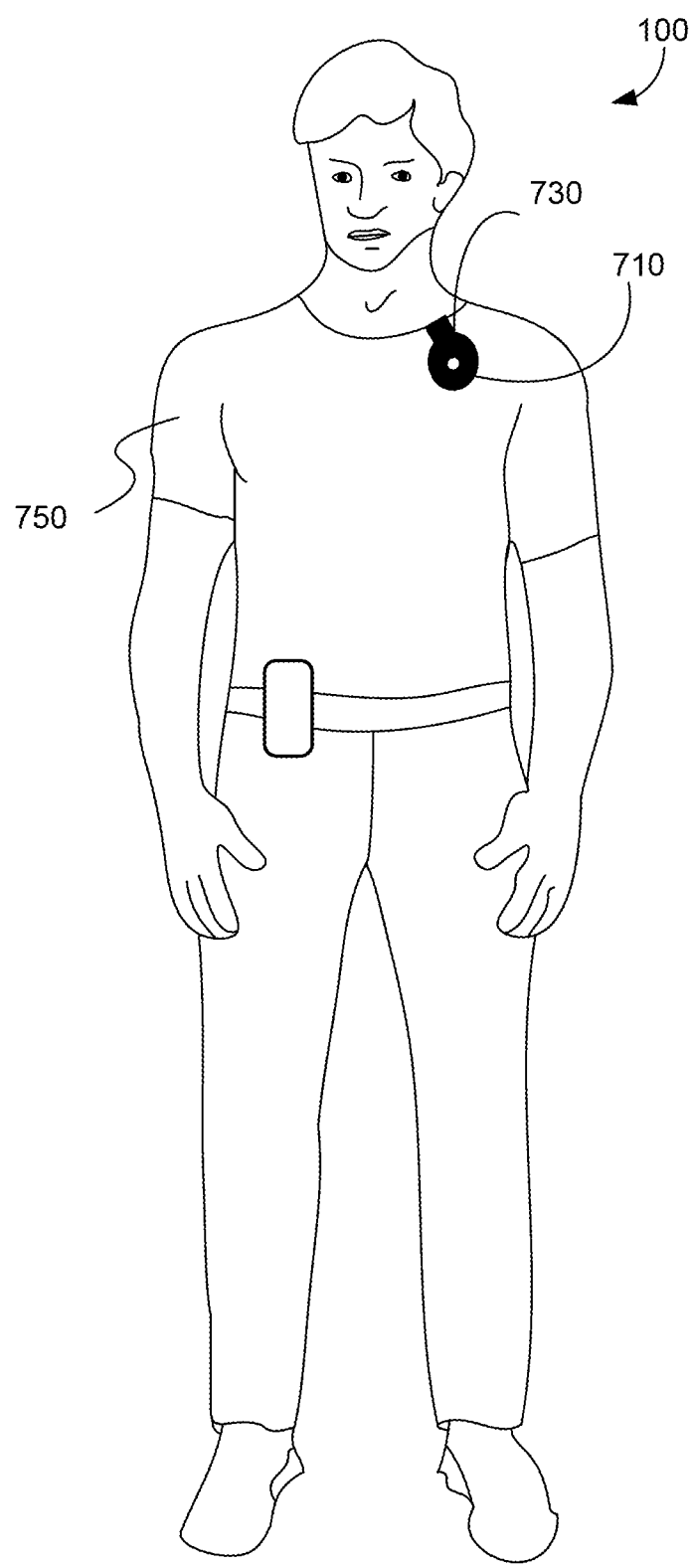
FIG. 9 is a schematic illustration of a user wearing a wearable apparatus consistent with an embodiment of the present disclosure.

FIG. 9 is a schematic illustration of a user 100 wearing a wearable apparatus 110 consistent with an embodiment of the present disclosure. As illustrated in FIG. 9, capturing unit 710 is located on an exterior surface of the clothing 750 of user 100. Capturing unit 710 is connected to power unit 720 (not seen in this illustration) via connector 730, which wraps around an edge of clothing 750.

Figure 10:
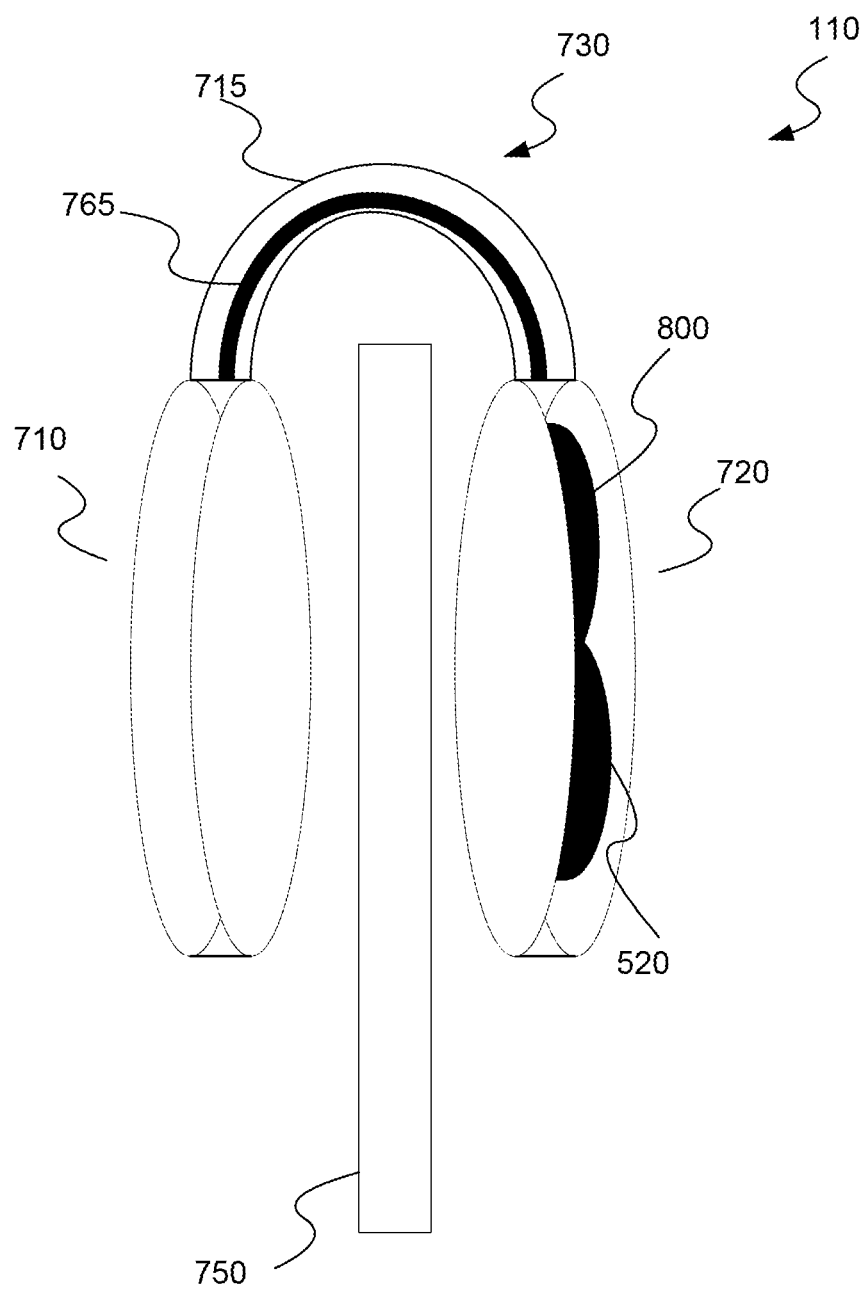
FIG. 10 is a schematic illustration of an embodiment of a wearable apparatus securable to an article of clothing consistent with the present disclosure.

In some embodiments, connector 730 may include a flexible printed circuit board (PCB). FIG. 10 illustrates an exemplary embodiment wherein connector 730 includes a flexible printed circuit board 765. Flexible printed circuit board 765 may include data connections and power connections between capturing unit 710 and power unit 720. Thus, in some embodiments, flexible printed circuit board 765 may serve to replace power cable 760 and data cable 770. In alternative embodiments, flexible printed circuit board 765 may be included in addition to at least one of power cable 760 and data cable 770. In various embodiments discussed herein, flexible printed circuit board 765 may be substituted for, or included in addition to, power cable 760 and data cable 770.

Figure 11:
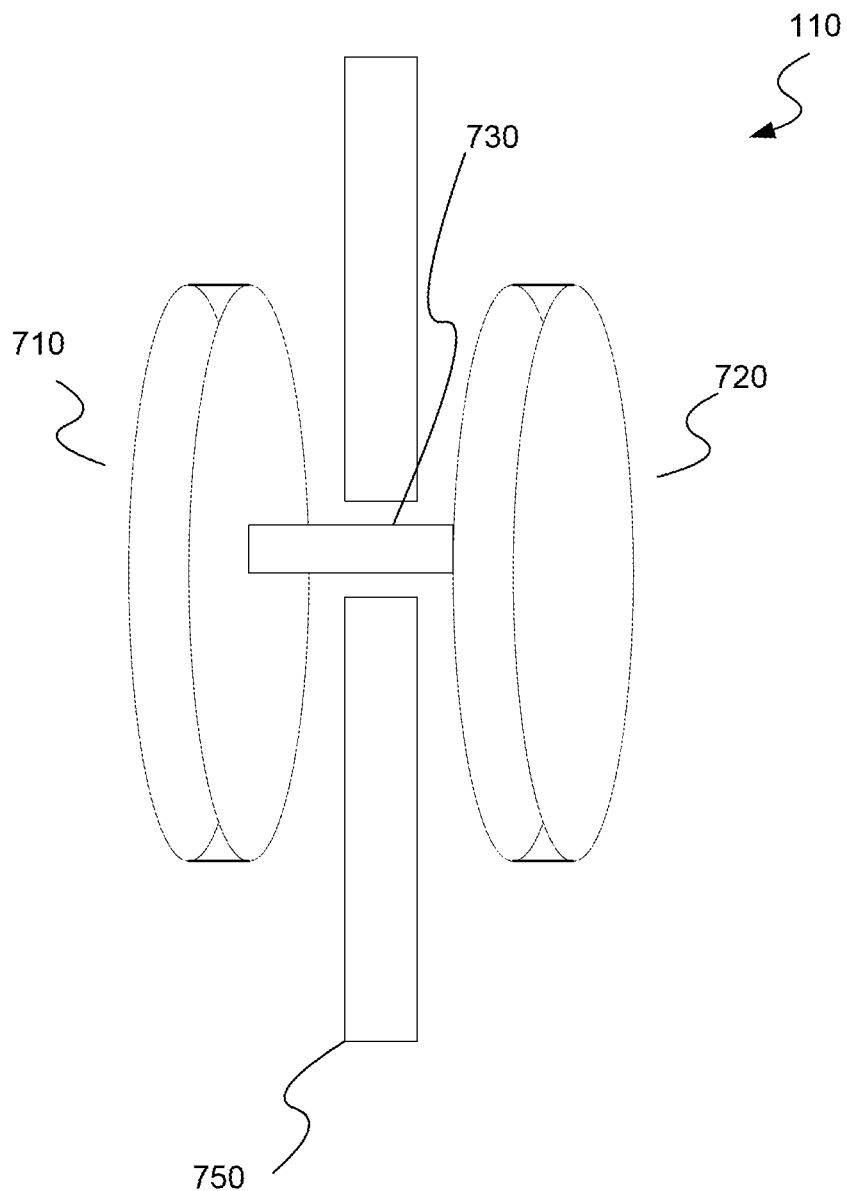
FIG. 11 is a schematic illustration of an embodiment of a wearable apparatus securable to an article of clothing consistent with the present disclosure.

FIG. 11 is a schematic illustration of another embodiment of a wearable apparatus securable to an article of clothing consistent with the present disclosure. As illustrated in FIG. 11, connector 730 may be centrally located with respect to capturing unit 710 and power unit 720. Central location of connector 730 may facilitate affixing apparatus 110 to clothing 750 through a hole in clothing 750 such as, for example, a button-hole in an existing article of clothing 750 or a specialty hole in an article of clothing 750 designed to accommodate wearable apparatus 110.

Figure 12:
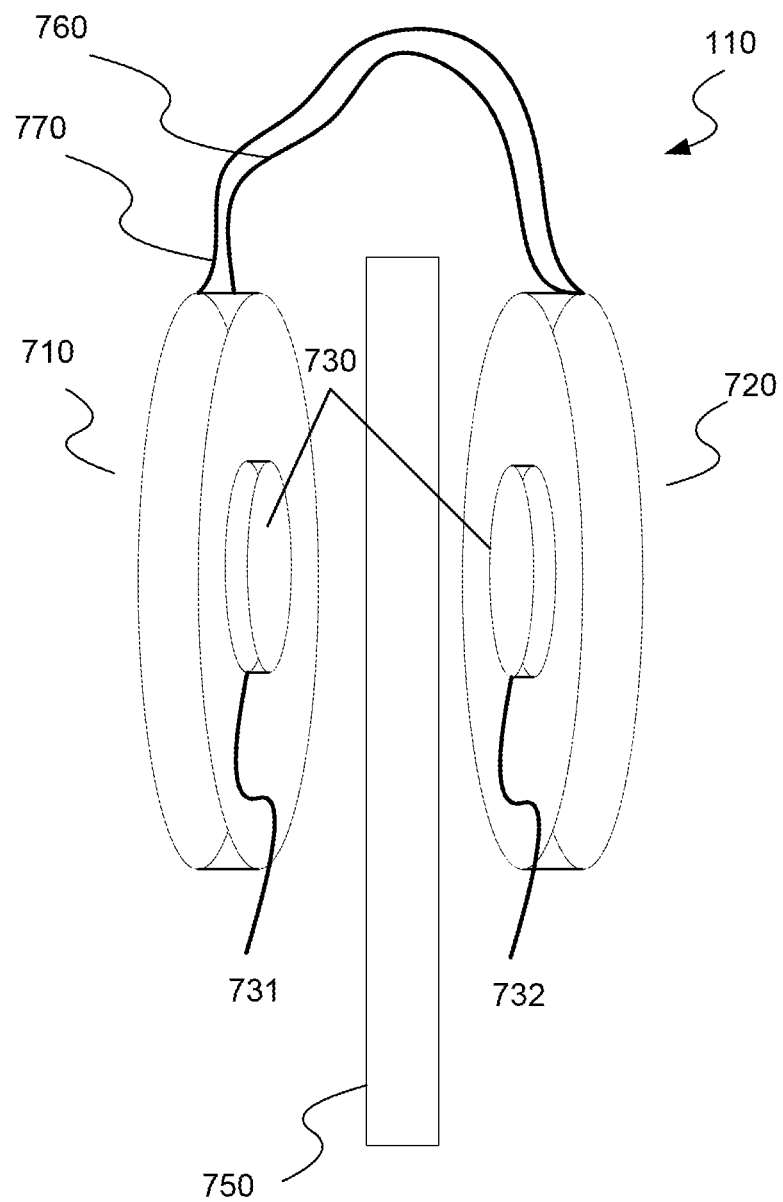
FIG. 12 is a schematic illustration of an embodiment of a wearable apparatus securable to an article of clothing consistent with the present disclosure.

FIG. 12 is a schematic illustration of still another embodiment of wearable apparatus 110 securable to an article of clothing. As illustrated in FIG. 12, connector 730 may include a first magnet 731 and a second magnet 732. First magnet 731 and second magnet 732 may secure capturing unit 710 to power unit 720 with the article of clothing positioned between first magnet 731 and second magnet 732. In embodiments including first magnet 731 and second magnet 732, power cable 760 and data cable 770 may also be included. In these embodiments, power cable 760 and data cable 770 may be of any length, and may provide a flexible power and data connection between capturing unit 710 and power unit 720. Embodiments including first magnet 731 and second magnet 732 may further include a flexible PCB 765 connection in addition to or instead of power cable 760 and/or data cable 770. In some embodiments, first magnet 731 or second magnet 732 may be replaced by an object comprising a metal material.

Figure 13:
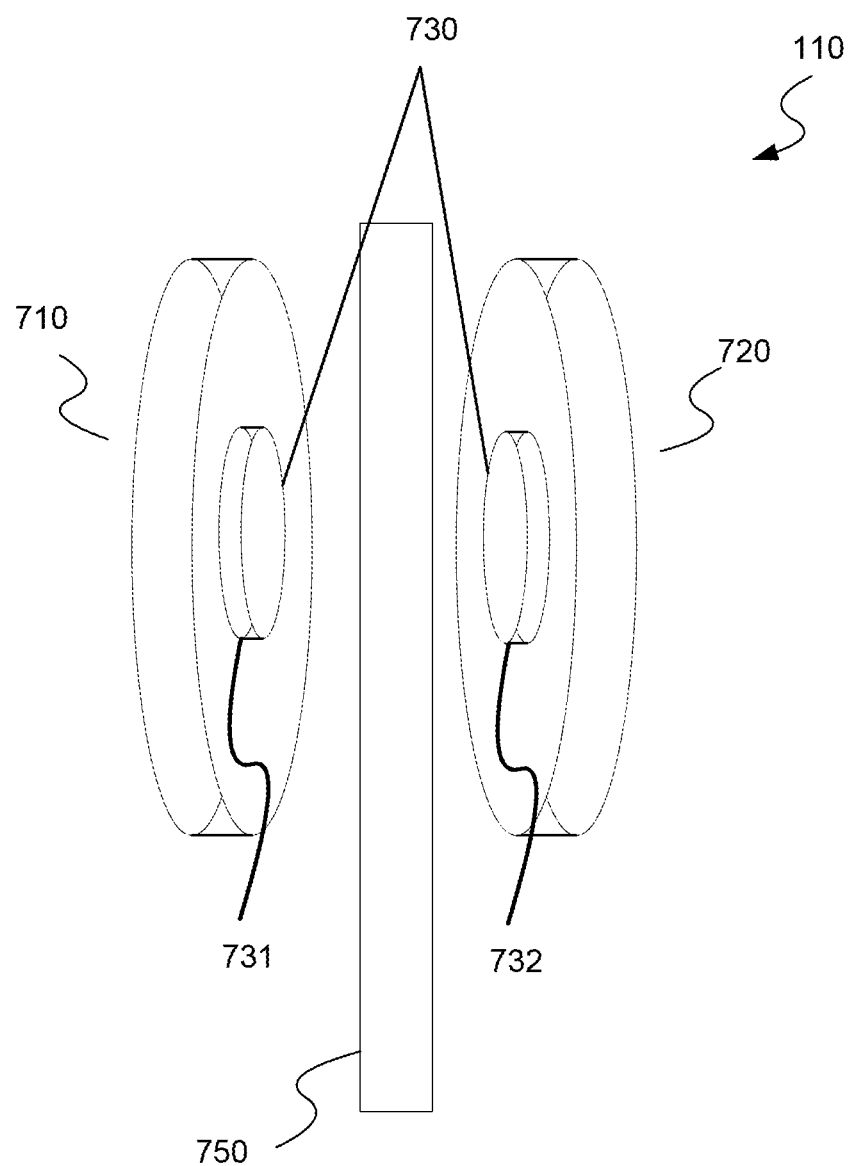
FIG. 13 is a schematic illustration of an embodiment of a wearable apparatus securable to an article of clothing consistent with the present disclosure.

FIG. 13 is a schematic illustration of yet another embodiment of a wearable apparatus 110 securable to an article of clothing. FIG. 13 illustrates an embodiment wherein power and data may be wirelessly transferred between capturing unit 710 and power unit 720. As illustrated in FIG. 13, first magnet 731 and second magnet 732 may be provided as connector 730 to secure capturing unit 710 and power unit 720 to an article of clothing 750. Power and/or data may be transferred between capturing unit 710 and power unit 720 via any suitable wireless technology, for example, magnetic and/or capacitive coupling, near field communication technologies, radiofrequency transfer, and any other wireless technology suitable for transferring data and/or power across short distances.

Figure 14:
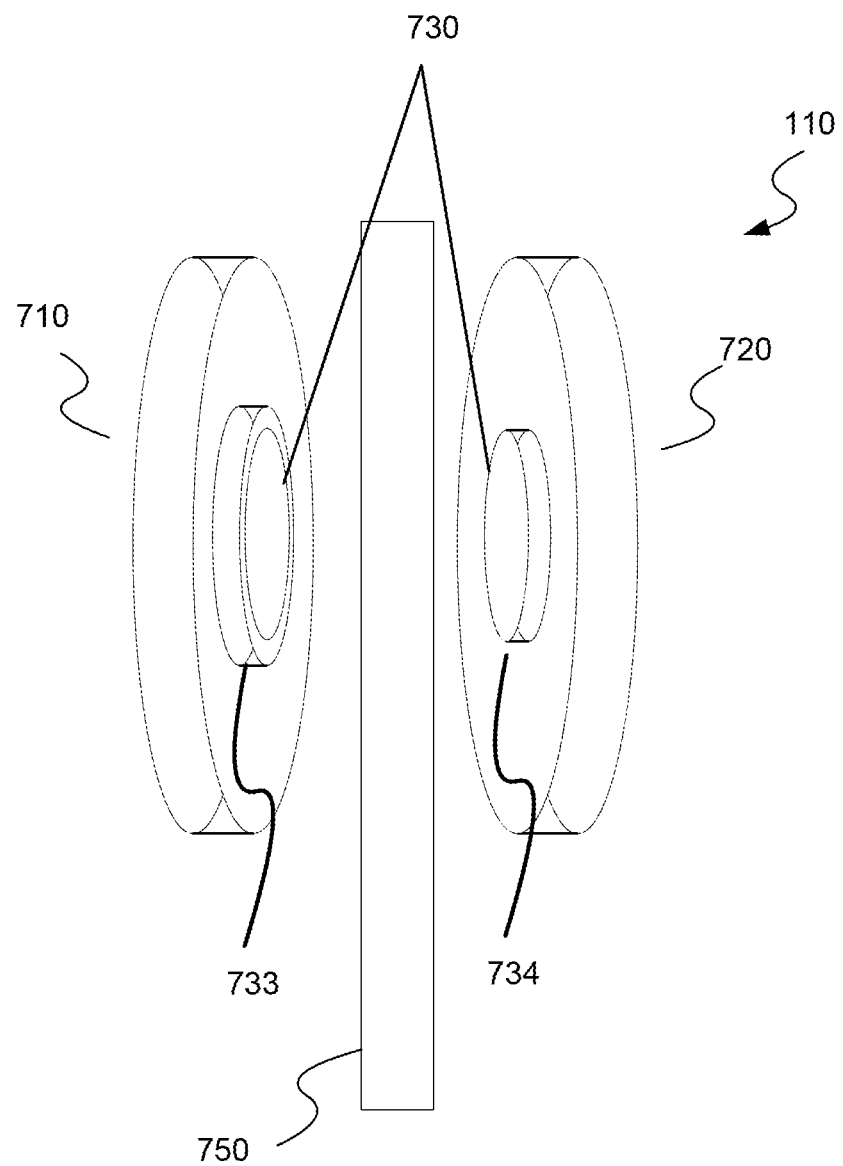
FIG. 14 is a schematic illustration of an embodiment of a wearable apparatus securable to an article of clothing consistent with the present disclosure.

FIG. 14 illustrates still another embodiment of wearable apparatus 110 securable to an article of clothing 750 of a user. As illustrated in FIG. 14, connector 730 may include features designed for a contact fit. For example, capturing unit 710 may include a ring 733 with a hollow center having a diameter slightly larger than a disk-shaped protrusion 734 located on power unit 720. When pressed together with fabric of an article of clothing 750 between them, disk-shaped protrusion 734 may fit tightly inside ring 733, securing capturing unit 710 to power unit 720. FIG. 14 illustrates an embodiment that does not include any cabling or other physical connection between capturing unit 710 and power unit 720. In this embodiment, capturing unit 710 and power unit 720 may transfer power and data wirelessly. In alternative embodiments, capturing unit 710 and power unit 720 may transfer power and data via at least one of cable 760, data cable 770, and flexible printed circuit board 765.

Figure 15:
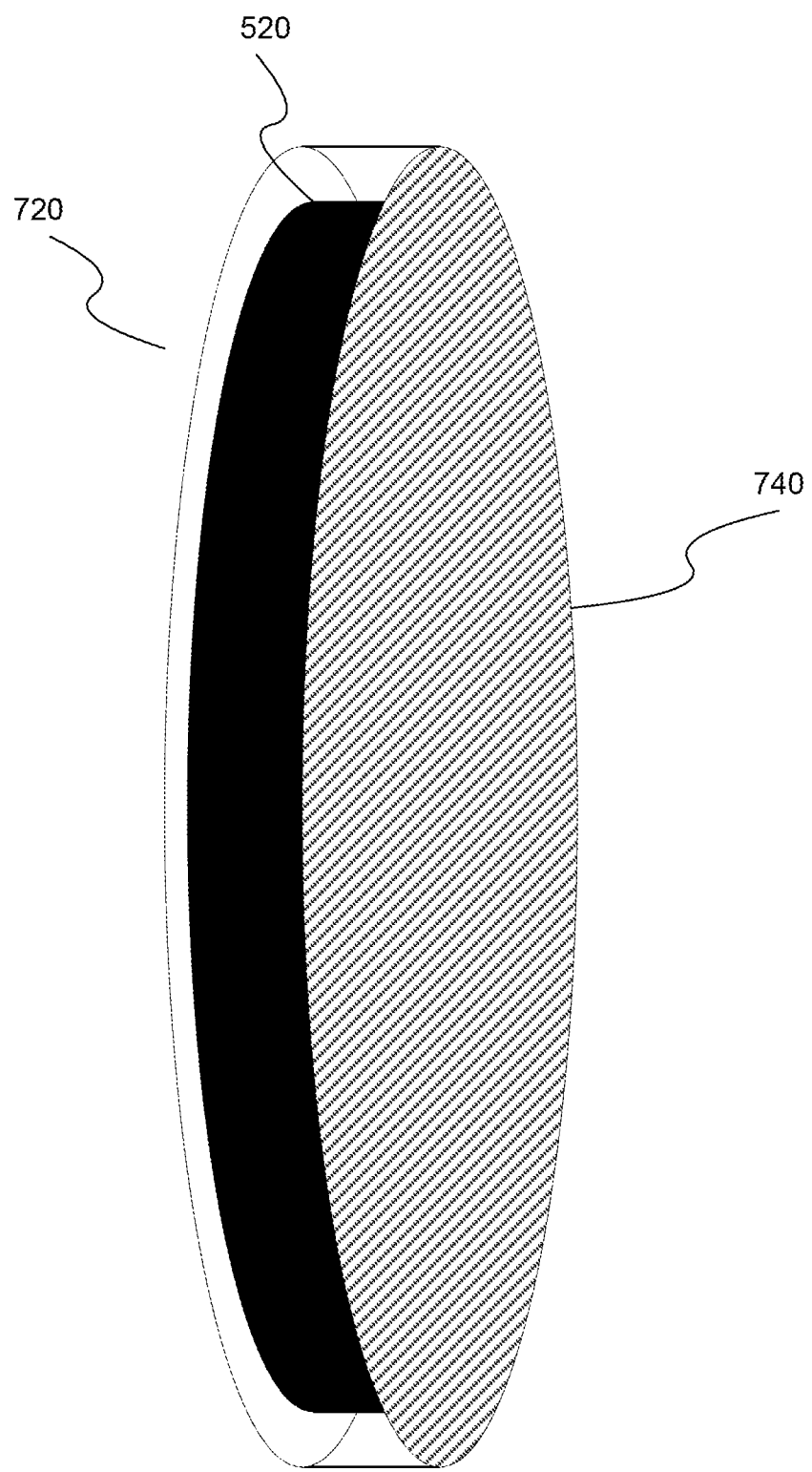
FIG. 15 is a schematic illustration of an embodiment of a wearable apparatus power unit including a power source.

FIG. 15 illustrates another aspect of power unit 720 consistent with embodiments described herein. Power unit 720 may be configured to be positioned directly against the user's skin. To facilitate such positioning, power unit 720 may further include at least one surface coated with a biocompatible material 740. Biocompatible materials 740 may include materials that will not negatively react with the skin of the user when worn against the skin for extended periods of time. Such materials may include, for example, silicone. PTFE, kapton, polyimide, titanium, nitinol, platinum, and others. Also as illustrated in FIG. 15, power unit 720 may be sized such that an inner volume of the power unit is substantially filled by mobile power source 520. That is, in some embodiments, the inner volume of power unit 720 may be such that the volume does not accommodate any additional components except for mobile power source 520. In some embodiments, mobile power source 520 may take advantage of its close proximity to the skin of user's skin. For example, mobile power source 520 may use the Peltier effect to produce power andor charge the power source.

Figure 16:
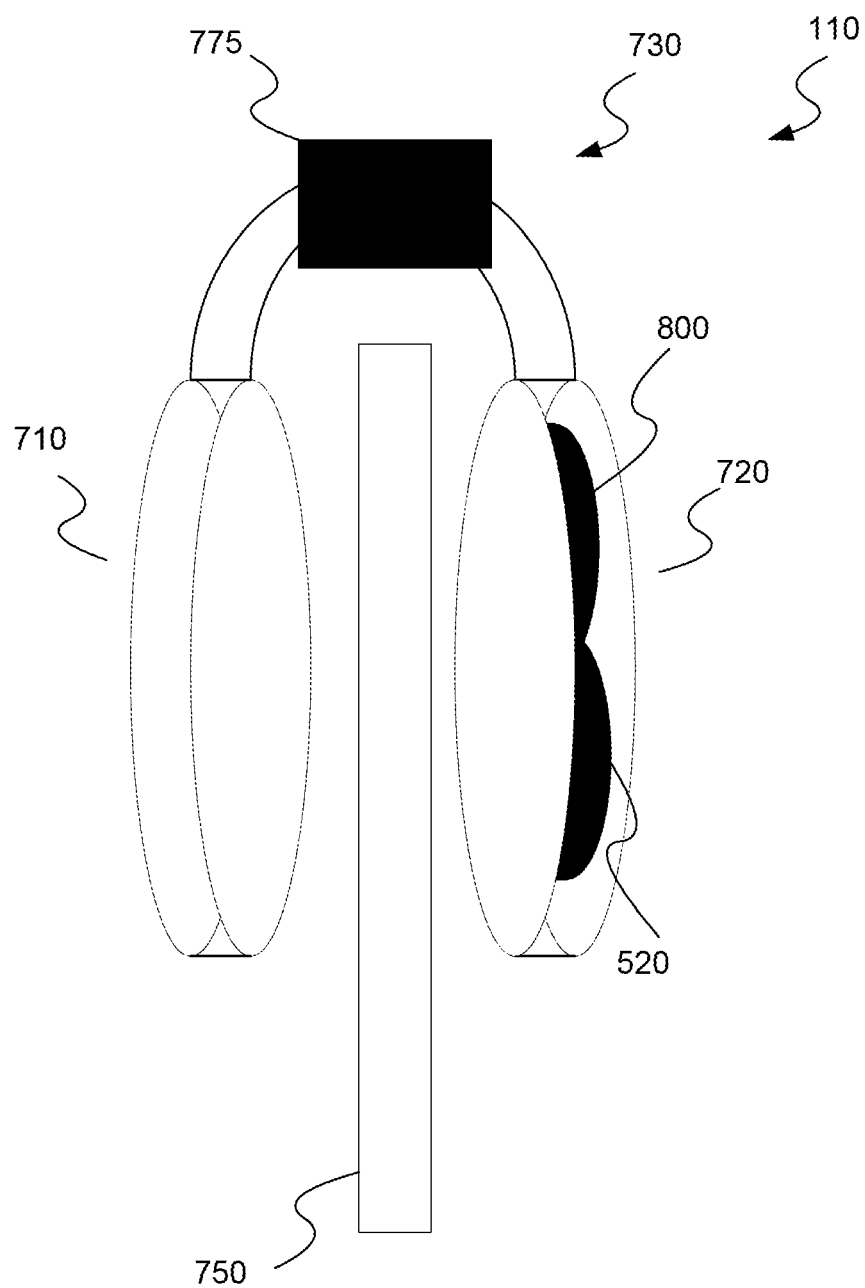
FIG. 16 is a schematic illustration of an exemplary embodiment of a wearable apparatus including protective circuitry.

In further embodiments, an apparatus securable to an article of clothing may further include protective circuitry associated with power source 520 housed in in power unit 720. FIG. 16 illustrates an exemplary embodiment including protective circuitry 775. As illustrated in FIG. 16, protective circuitry 775 may be located remotely with respect to power unit 720. In alternative embodiments, protective circuitry 775 may also be located in capturing unit 710, on flexible printed circuit board 765, or in power unit 720.

Protective circuitry 775 may be configured to protect image sensor 220 and/or other elements of capturing unit 710 from potentially dangerous currents andor voltages produced by mobile power source 520. Protective circuitry 775 may include passive components such as capacitors, resistors, diodes, inductors, etc., to provide protection to elements of capturing unit 710. In some embodiments, protective circuitry 775 may also include active components, such as transistors, to provide protection to elements of capturing unit 710. For example, in some embodiments, protective circuitry 775 may comprise one or more resistors serving as fuses. Each fuse may comprise a wire or strip that melts (thereby braking a connection between circuitry of image capturing unit 710 and circuitry of power unit 720) when current flowing through the fuse exceeds a predetermined limit (e.g., 500 milliamps, 900 milliamps, 1 amp, 1.1 amps, 2 amp, 2.1 amps, 3 amps, etc.). Any or all of the previously described embodiments may incorporate protective circuitry 775.

In some embodiments, the wearable apparatus may transmit data to a computing device (e.g., a smartphone, tablet, watch, computer, etc.) over one or more networks via any known wireless standard (e.g., cellular, Wi-Fi, Bluetooth®, etc.), or via near-field capacitive coupling, other short range wireless techniques, or via a wired connection. Similarly, the wearable apparatus may receive data from the computing device over one or more networks via any known wireless standard (e.g., cellular, Wi-Fi, Bluetooth®, etc.), or via near-field capacitive coupling, other short range wireless techniques, or via a wired connection. The data transmitted to the wearable apparatus and or received by the wireless apparatus may include images, portions of images, identifiers related to information appearing in analyzed images or associated with analyzed audio, or any other data representing image and/or audio data. For example, an image may be analyzed and an identifier related to an activity occurring in the image may be transmitted to the computing device (e.g., the "paired device"). In the embodiments described herein, the wearable apparatus may process images and/or audio locally (on board the wearable apparatus) and/or remotely (via a computing device). Further, in the embodiments described herein, the wearable apparatus may transmit data related to the analysis of images and/or audio to a computing device for further analysis, display, and or transmission to another device (e.g., a paired device). Further, a paired device may execute one or more applications (apps) to process, display, and or analyze data (e.g., identifiers, text, images, audio, etc.) received from the wearable apparatus.

Some of the disclosed embodiments may involve systems, devices, methods, and software products for determining at least one keyword. For example, at least one keyword may be determined based on data collected by apparatus 110. At least one search query may be determined based on the at least one keyword. The at least one search query may be transmitted to a search engine.

In some embodiments, at least one keyword may be determined based on at least one or more images captured by image sensor 220. In some cases, the at least one keyword may be selected from a keywords pool stored in memory. In some cases, optical character recognition (OCR) may be performed on at least one image captured by image sensor 220, and the at least one keyword may be determined based on the OCR result. In some cases, at least one image captured by image sensor 220 may be analyzed to recognize: a person, an object, a location, a scene, and so forth. Further, the at least one keyword may be determined based on the recognized person, object, location, scene, etc. For example, the at least one keyword may comprise: a person's name, an object's name, a place's name, a date, a sport team's name, a movie's name, a book's name, and so forth.

In some embodiments, at least one keyword may be determined based on the user's behavior. The user's behavior may be determined based on an analysis of the one or more images captured by image sensor 220. In some embodiments, at least one key word may be determined based on activities of a user and or other person. The one or more images captured by image sensor 220 may be analyzed to identify the activities of the user and/or the other person who appears in one or more images captured by image sensor 220. In some embodiments, at least one keyword may be determined based on at least one or more audio segments captured by apparatus 110. In some embodiments, at least one keyword may be determined based on at least GPS information associated with the user. In some embodiments, at least one keyword may be determined based on at least the current time and or date.

In some embodiments, at least one search query may be determined based on at least one keyword. In some cases, the at least one search query may comprise the at least one keyword. In some eases, the at least one search query may comprise the at least one keyword and additional key words provided by the user. In some cases, the at least one search query may comprise the at least one key word and one or more images, such as images captured by image sensor 220. In some cases, the at least one search query may comprise the at least one keyword and one or more audio segments, such as audio segments captured by apparatus 110.

In some embodiments, the at least one search query may be transmitted to a search engine. In some embodiments, search results provided by the search engine in response to the at least one search query may be provided to the user. In some embodiments, the at least one search query may be used to access a database.

For example, in one embodiment, the keywords may include a name of a type of food, such as quinoa, or a brand name of a food product; and the search will output information related to desirable quantities of consumption, facts about the nutritional profile, and so forth. In another example, in one embodiment, the keywords may include a name of a restaurant, and the search will output information related to the restaurant, such as a menu, opening hours, reviews, and so forth. The name of the restaurant may be obtained using OCR on an image of signage, using GPS information, and so forth. In another example, in one embodiment, the keywords may include a name of a person, and the search will provide information from a social network profile of the person. The name of the person may be obtained using OCR on an image of a name tag attached to the person's shin, using face recognition algorithms, and so forth. In another example, in one embodiment, the keywords may include a name of a book, and the search will output information related to the book, such as reviews, sales statistics, information regarding the author of the hook, and so forth. In another example, in one embodiment, the keywords may include a name of a movie, and the search will output information related to the movie, such as reviews, box office statistics, information regarding the cast of the movie, show times, and so forth. In another example, in one embodiment, the keywords may include a name of a sport team, and the search will output information related to the sport team, such as statistics, latest results, future schedule, information regarding the players of the sport team, and so forth. For example, the name of the sport team may be obtained using audio recognition algorithms.

In some embodiments, wearable apparatus 110 may monitor consumption of a user and provide feedback relating to the consumption. For example, wearable apparatus 110 may automatically monitor the consumption of a user by analyzing images captured from an environment of the user. The images may be captured by at least one image capture device configured to capture a plurality of images from the environment of user 100 of wearable apparatus 110. For example, the at least one image capture device may include image sensor 220 or a video camera or a combination thereof. It is contemplated that plurality of images may be captured by a plurality of image capture devices. For example, user 100 may wear more than one wearable apparatus 110 or may wear one wearable apparatus 110 and have a second means for capturing images of his or her environment. In some embodiments, wearable apparatus 110 may include at least one processing device. For example, wearable apparatus 110 may include processor 210, which may be configured to monitor consumption of user 100. By way of example, processor 210 may be configured to analyze the images captured by the one or more image capture devices and to detect consumable objects in one or more images. In some embodiments, wearable apparatus 110 may be paired to another device (e.g., a smartphone, tablet, smartwatch, or the like). The other device may be configured to perform all or a portion of the method for monitoring consumption of a user.

Figure 17:
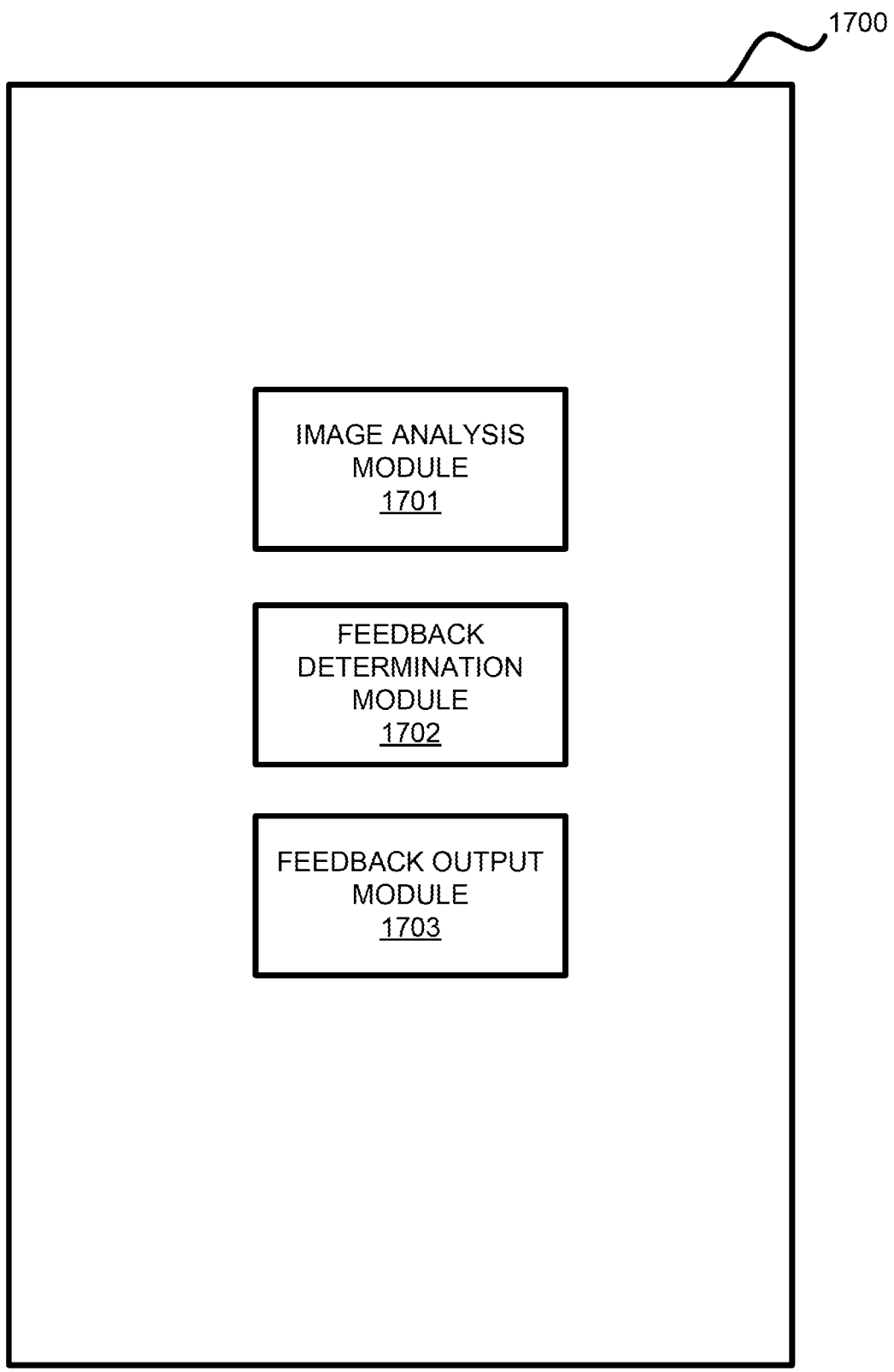
FIG. 17 illustrates an exemplary embodiment of a memory containing software modules consistent with the present disclosure.

FIG. 17 illustrates an exemplary embodiment of a memory 1700 containing modules consistent with the present disclosure. Memory 1700 may be included in wearable apparatus 110 (e.g., as memory 550a), may be included in another device in communication with wearable apparatus 110 (e.g., in computing device 120), or may be a stand-alone device. An analysis module, such as image analysis module 1701, may be included in memory 1700. A feedback determination module 1702 and/or a feedback output module 1703 may be included in memory 1700. Each module 1701, 1702, and 1703 may contain software instructions for performing all or a portion of a method for monitoring consumption of a user and providing feedback related thereto. The instructions may be executed by a processing device, such as processor 210 and or processor 540, included in wearable apparatus 110 or computing device 120, respectively.

Image analysis module 1701 may include instructions for identifying at least one consumption indicator from one or more images. A consumption indicator may be identified, for example, by analyzing one or more images for a known indicator of consumption. For example, a consumption indicator may be an object such as a spoon, fork, cup, glass, cigarette, cigar, a piece of food, a snack, a menu, a pill bottle, or the like. The consumption indicator may also be associated with gestures or movement of a user that are indicative of consumption. For example, the consumption indicator may include movement of a hand, utensil, cup, or other object to and from the mouth, or movement of the jaws in a chewing pattern, or other movement associated with consumption. The consumption indicator may also include audible indicators, such as noises associated with chewing, swallowing, or the like. Consistent with this disclosure, one or more consumption indicators may be detected by analysis of one or more images, a video, or a combination thereof. Detection of a consumption indicator may initiate the automatic monitoring of consumption and trigger other actions related to identifying the type and amount of consumable product consumed and providing feedback based on the consumption.

In some embodiments, one or more algorithms may be used to detect consumption. For example, a consumption recognition algorithm may be configured to access a database containing known consumables and to compare captured images with the known consumable to accurately detect a consumable product and to detect a type of the consumable product. As an example, image processing module 1701 may include instructions for detecting a consumption indicator, such as a gesture associated with consumption, and being analyzing images received from an image capture device to detect consumable products. When an object that may be a consumable product is detected, image analysis module 1701 may include instructions for accessing a database, for example, and comparing the object with known consumables to confirm that the detected object is a consumable product. The database may be included in the wearable apparatus or accessed over a network (e.g., a remote server). The type of the consumable product may be determined in substantially the same manner. For example, image analysis module 1701 may include instructions for comparing a captured image with a plurality of known consumable products to determine that, for example, the object detected in the image is a hamburger. Image analysis module 1701 may include instructions for comparing the image of the detected hamburger with a plurality of known hamburger types to determine the type of the hamburger. For example, one or more captured images may be compared with known images of hamburgers. The type of the hamburger may be, for example, a brand name associated with the hamburger or a break down of the components on the hamburger. Image analysis module 1701 may include instructions for detecting a consumable product and may determine a type of the detected consumable product by any means disclosed herein. Consistent with this disclosure, image analysis module 1701 may include instructions for performing other operations for determining an amount of a consumable product that a person has consumed, the amount of calories or nutrients consumed, or the like.

Feedback determination module 1702 may include instructions for processing the data collected and generated by the operations of image analysis module 1701 and determining a feedback for the user. For example, feedback determination module 1702 may include instructions for determining a feedback based on the type indicator of the detected consumable product and the estimated amount of the consumable product consumed by the user. In some embodiments, the estimated amount of the consumable product consumed by the user may include an amount of calories or nutrients consumed by a user, or a quantity of a particular item (e.g. three cookies). For example, nutrition information for a detected type of consumable may be accessed through a network or from a database and used to determine the amount of fat, protein, carbohydrates, sodium, cholesterol, etc. consumed by the user. It is also contemplated that feedback determination module 1702 may include instructions for accessing user settings, preferences, or goals and determine feedback based thereon. For example, a user may indicate in user preferences a maximum number of calories he or she intends to consume during a meal, day, week, month, or other time frame and feedback determination module 1702 may include instructions for determining how a consumed amount of calories compares to the maximum and determine a feedback consistent with the comparison. The feedback determined by the operations of feedback determination module 1702 may be any consistent with this disclosure.

Feedback output module 1703 may include instructions for providing the feedback determined by the operations of feedback determination module 1702 to an outputting unit. For example, feedback output module 1703 may provide the feedback for output to a display, speaker, or vibration motor of wearable apparatus 110, a display, speaker, or vibration motor of computing device 120, any other device in communication with processing device 1700, or the like. The feedback may be transmitted directly for output or stored in a memory for later output, or a combination thereof. For example, the feedback may be stored in a memory, such as memory 550 or 550b, where it may be aggregated over time and the aggregated feedback may be output at a later time or used to determine further feedback or the like. As another example, the feedback may be transmitted directly to an outputting unit, such as feedback outputting unit 230 or 545. The feedback may be output by any means disclosed herein.

Consistent with this disclosure, wearable apparatus 110 may be configured to capture a plurality of images of a users environment. For example, wearable apparatus 110 may be worn by user 100 in any manner disclosed herein and may capture images of the field of view of user 100. In another example, wearable device 110 may be worn by user 100 and may be configured to focus on an object or area of interest within an environment, as described above, and may capture images of the object or area. For example, image sensor 220 may be focused on a table, plate, hand, utensil, or other object related to consumption and the images captured may include representations of consumable products. As discussed above, the environment may include any area around the user, the field of view of the user, or an area of interest within view of image sensor 220 of wearable apparatus 110.

Figure 18:
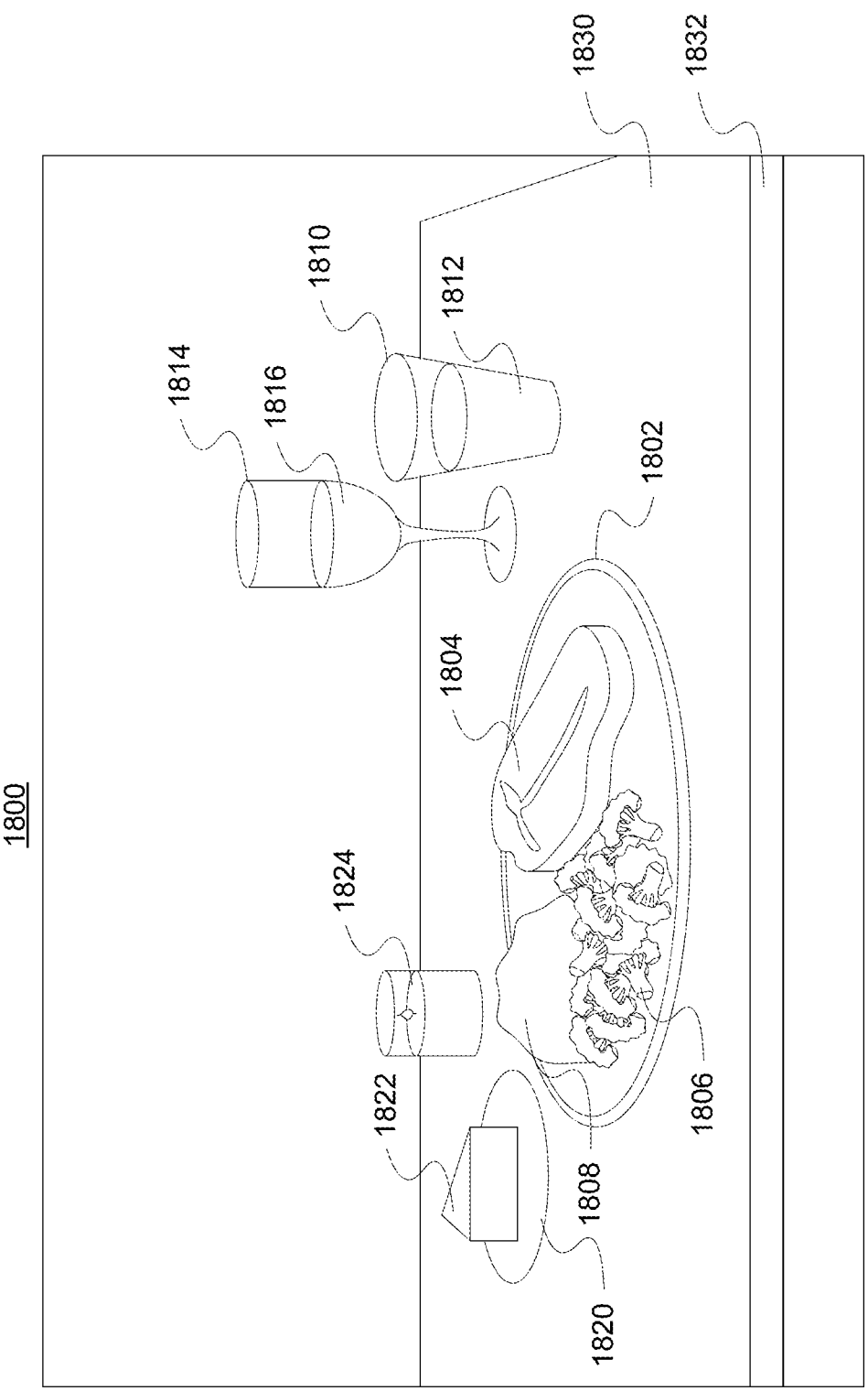
FIG. 18 is a schematic illustration of an image that may be analyzed by a wearable apparatus consistent with the present disclosure.
Figure 19:
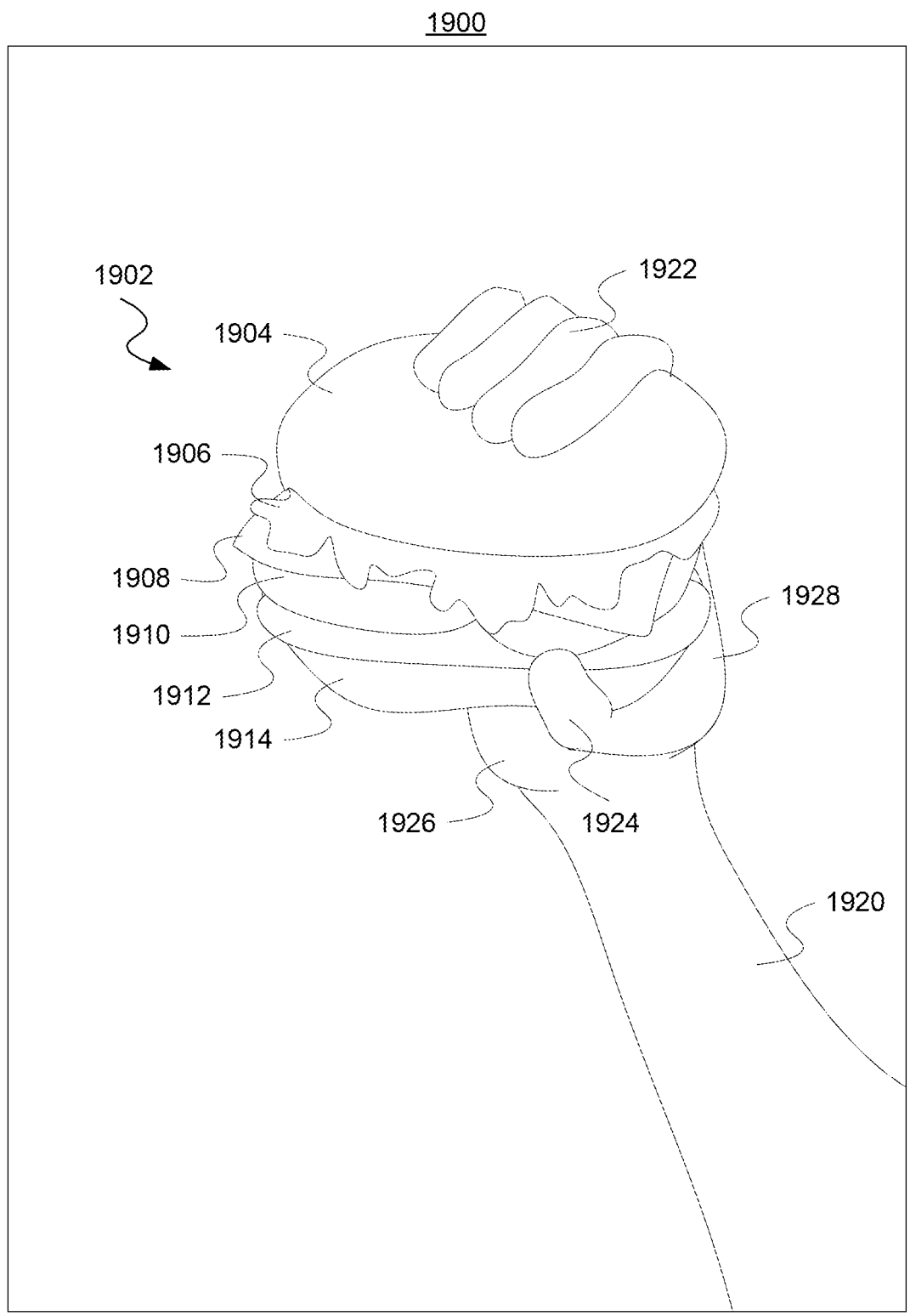
FIG. 19 is another schematic illustration of an exemplary image that may be analyzed by a wearable apparatus consistent with the present disclosure.

FIG. 18 is an illustrative example of an image 1800 that may be captured by wearable apparatus 110. Image 1800 includes several objects, both consumable and non-consumable, located on a table 1830. Images similar to image 1800 may be captured when, for example, user 100 is wearing wearable apparatus 110 while dinning in a restaurant or another location. FIG. 19 is another illustrative example of an image 1900 that may be captured by wearable apparatus 110. Image 1900 includes a representation of an arm 1920 and a hand 1928 belonging to user 100, and a cheeseburger 1902 in hand 1928. Images similar to image 1900 may be captured by wearable apparatus, for example, as user 100 is bringing an object, such as cheeseburger 1902, to his or her mouth. FIG. 18 and FIG. 19 illustrate examples of the present disclosure. It is understood that they are not limiting in any way and the images captured by wearable apparatus 110 may be substantially different from either image 1800 or image 1900.

The images may be captured in response to detection of a consumption indicator, as discussed above. For example, wearable apparatus 110 may be configured to begin capturing images of user's 100 environment in response to detection of chewing, swallowing, or other action associated with consumption. In some embodiments, wearable apparatus 110 may be configured to periodically capture images of a user's environment and be further configured to capture images of the environment more frequently after detection of a consumption indicator. For example, wearable apparatus 110 may capture images of the environment at a predetermined interval (e.g., every second, every five seconds, every ten seconds, every fifteen seconds, etc.) and when a consumption indicator, such as a fork, cup, cigarette carton, etc. is detected in one of the images, wearable apparatus 110 may be configured to increase the rate of image capture to a predetermined rate (e.g., such that it is capturing images every second, every half-second, every tenth of a second, etc.). The time intervals are exemplary only and not limiting. In another embodiment, wearable apparatus 110 may be configured to continuously capture images or video of the environment and to continuously monitor for consumable products.

Consistent with this disclosure, the at least one processing device may be configured to analyze a plurality of images to detect a consumable product represented in at least one of the plurality of images. As discussed above, the plurality of images may be captured by wearable apparatus 110, for example by image sensor 220. It is also contemplated that the plurality of images may be captured by another device (for example, a second wearable apparatus 110) and transmitted to wearable apparatus 110. It is further contemplated that the plurality of images may be captured by one or more wearable apparatus 100 and the images or data relating thereto may be transmitted to computing device 120 or another device for processing (e.g., a remote server accessible over one or more networks). In some embodiments, the plurality of images may be received by wearable apparatus 110 or computing device 120 and analyzed to detect consumable products.

In some embodiments, the at least one processing device may use one or more image analysis algorithms or image analysis techniques to detect consumable products. For example, detection of a consumable product may be accomplished by appearance-based algorithms, template-matching based algorithms, skeletal based algorithms, color-recognition algorithms, machine-learning based algorithms, neural-network based algorithms, vector analysis algorithms, and so forth. In another example, detection of a consumable product may be accomplished using image enhancement, edge detection, data extraction, and so forth. For example, wearable apparatus may compare the representation of objects in captured image with images of objects of known types. The images used for comparison may be stored on a memory (e.g., memory 550 or 550b) or may be stored in and accessed from a database (e.g., a local database local to the wearable apparatus and/or a remote database accessible over one or more networks). The images used for comparison may include additional information, such as an indicator of types of consumable products commonly associated with those objects. This information may aid in determining a type of a detected consumable product, as described below.

A consumable product may be detected directly or may be detected based on its relation to an object associated with consumption. For example, a consumable product may be detected by first detecting a plate or cup resting on a table and then detecting an object on the plate or in the cup. The object associated with consumption may be identified by comparison of the object with images of objects of a known type. For example, when analyzing image 1800, wearable apparatus 110 may detect objects 1810 and 1814. By comparing the general shape, size, and visual appearance of objects 1810 and 1814 with images of known objects, wearable apparatus 110 may determine that object 1810 is a glass and object 1814 is a wine glass. Based on the comparison, wearable apparatus 110 may detect that liquid 1812 and 1816 are consumable products. As another example, wearable apparatus may detect object 1824 in image 1800 and determine, by substantially the same process, that object 1824 is a candle. Based on this determination, wearable apparatus 110 may determine that the contents of candle 1824 are not consumable products.

In another example, the at least one processing device may directly identify a consumable object. For example, wearable apparatus 110 may directly detect a consumable product by, for example, identifying an object having the same shape or appearance as a known consumable product. For example, in image 1800, wearable apparatus 110 may detect object 1822 and determine (e.g., based on its distinctive shape, a comparison with known objects, etc.) that object 1822 is a consumable product. It is also contemplated that wearable apparatus 110 may determine that object 1822 is a dessert or, more specifically, a piece of cake. On the other hand, wearable apparatus 110 may determine that object 1820 is a plate and is not consumable.

In some embodiments, the at least one processing device may be configured to detect a plurality of consumable products and differentiate between those products. For example, while analyzing image 1800, wearable apparatus 100 may identify object 1802 and properly classify it as a plate. Wearable apparatus 110 may then detect the objects located on plate 1802 and determine that they are consumable products. Wearable apparatus 110 may identify three objects 1804, 1808, and 1806 on plate 1802. The objects 1804, 1808, and 1806 may be identified based on an analysis of the outline of each object, of the shapes related with each object, of the color associated with each object, and so forth. For example, wearable apparatus 110 may detect a first object 1804 and differentiate it from the other objects on plate 1802 based on the relative shape, size, texture, or other visual appearance of object 1804. The same may be true for objects 1808 and 1806. Wearable apparatus 110 may further be configured to recognize that some consumable products may be comprised of a plurality of objects. For example, wearable apparatus 110 may be able to recognize that object 1808 is a single mass and that object 1806 is comprised of several components. The components of object 1806 may be identified as belonging to object 1806 based on, for example, each component being more similar to the other components of object 1806 than they are to other objects in the vicinity, such as object 1804 or object 1808.

In some embodiments, the at least one processing device may determine that an object is a consumable product based on its association with a consumption indicator. For example, as described above, certain movements of user 100, such as bringing a hand or utensil near the mouth repeatedly, are indicators of consumption. When analyzing image 1900, wearable apparatus 110 may determine that hand 1928 is approaching user 100's mouth. This may be based on, for example, a determination that hand 1928 is closer to the mouth than typical or that it is closer to the mouth than in an image captured just prior to image 1900. Based on the detection of the consumption indicator, wearable apparatus 110 may determine that an object in hand 1928 is a consumable product. Wearable apparatus 110 may then analyze image 1900 to detect the outline of hand 1928, including fingers 1922, thumb 1924, or palm 1926 and detect other objects not related to hand 1928. The other objects, here object 1902, may be determined to be a consumable product. It is also contemplated that wearable apparatus may detect object 1902 directly, as described above.

External information, such as location coordinates, schedule information, historical information, textual cues, audio cues, or the like, may aid in detection of a consumable product. For example, wearable apparatus 110 may receive location information relating to where user 100 is located in space. If user 100 is in a restaurant or other location associated with consumption, wearable apparatus 110 may be configured to assume that at least some objects detected at that location are consumable products. In another example, wearable apparatus 110 may access, for example, schedule information relating to a reservation user 100 has at a restaurant and may be configured to determine that at least some objects detected during the time of the reservation are consumable products. In another example, wearable apparatus 110 may access historical data relating to previous instances wherein a consumable product was detected, determine a pattern related thereto, and determine that objects detected consistent with that pattern are consumable objects. For example, if user 100 has a cigarette break at a similar time every day, wearable apparatus 110 may detect the consumption of a cigarette a plurality of times and determine a pattern relating to where and when the cigarette has been consumed. On later dates, wearable apparatus 110 may use that information to aid in detecting a cigarette consumed under circumstances with conditions similar to the determined pattern.

Consistent with this disclosure, the at least one processing device may be configured to, based on the detection of the consumable product represented in at least one of the plurality of images, determine a type indicator associated with the detected consumable product. The type indicator may be determined by analyzing one or more of the plurality of images. A type indicator may be an indication of the brand name, category, or other classification of the consumable product. For example, the type indicator associated with a detected consumable product may be food, beverage, alcoholic drink, pill, cigarette, or cigar. The type indicator may be more specific. For example, the type indicator associated with a detected consumable product may be soup, pasta, salad, bread, cake, dessert, vegetable, or meat. As may be appreciated from this disclosure, the type indicator may be an indicator associated with any level of categorization.

In some embodiments, the at least one processing device may be configured to determine the type indicator associated with the detected consumable product by comparing at least a portion of a plurality of images to stored images of known consumable product types. For example, an image representing a detected consumable product may be compared to images of known consumable products. The comparison may be carried out in substantially the same manner as described above. The images of the known consumable products may be stored on wearable apparatus 110, on computing device 120, or on another device in communication with wearable apparatus 110 or computing device 120. Additionally or alternatively, images of known consumable products may not be stored in a memory, but may be access by a search performed on the Internet, an intranet, or other online service. In some embodiments, the detected product may be determined to be of the type of the known consumable product represented in the image that most closely matches the image of the detected product. For example, a detected product may be compared to images depicting a hamburger, a cheeseburger, a chicken burger, and a grilled cheese, and may be determined to be, for example, a cheeseburger based on the image representing the detected product most closely matching the image of the cheeseburger.

In some embodiments, the at least one processing device may compare an image of a detected product to a plurality of images of known products in a number of rounds to determine a type of the detected product. The number of comparisons performed may depend on the level of specificity required or desired. For example, in the example of image 1800, wearable apparatus 110 may compare the representation of object 1808 (which was previously determined to be a consumable product on plate 1902) to a plurality of images representing a plurality of consumable products on plates. This first comparison may lead to a determination that object 1808 is a mashed consumable product. Wearable apparatus 110 may then compare object 1808 to a plurality of images of mashed consumable products. This comparison may lead to a determination that object 1898 is a mashed vegetable product. Wearable apparatus 110 may then compare object 1808 to a plurality of images of mashed vegetable products and, based on this comparison, ultimately determine that object 1808 is a pile of mashed sweet potatoes.

In some embodiments, the at least one processing device may be configured to use information relating to the detected product to determine a plurality of images to use for comparison in determining a type of the product. The information may be used to determine one or more keywords and the keywords may be used to locate images of known consumable products relating to the detected consumable product. The keywords may be determined as described above. As an example, wearable apparatus 110 may detect liquid 1816 by detecting wine glass 1814, as described above. Wearable apparatus 110 may then generate keywords related to wine glasses to search for images of consumable liquids in wine glasses. The images of liquids in wine glasses may then be compared to image 1800 (or the portion thereof containing wine glass 1814) to determine a type associated with liquid 1816. For example, after relatively few comparisons, wearable apparatus may determine that liquid 1816 is a Merlot based on its visual appearance matching that of an image of Merlot. This is advantageous because the at least one processing device may avoid unnecessary comparisons, such as a comparison of liquid 1816 to soup or to milk. It is contemplated that additional information may be used to generate keywords to further simplify the comparison process. Continuing the above example, wearable apparatus 110 may identify liquid 1816 as having a purplish-red color, which may be used to limit the images used for comparison to images of red wines, thereby preventing the use of time and processing power comparing liquid 1816 to white wines or other liquids that are unlikely to match liquid 1816. As another example, wearable apparatus 110 may identify a particular item (e.g., food or beverage) based on one or more images captured by wearable apparatus 110 that include a menu. For example, wearable apparatus 110 may use OCR techniques to identify text from the memory and/or may analyze captured audio data of the user placing an order.

In some embodiments, the detected product may not closely match any of the images of known consumable products. In this instance, the at least one processing device may be configured to determine the type of the detected consumable by identifying ingredients making up the detected consumable product. For example, if wearable apparatus 110 is not able to determine that cheeseburger 1902 is a cheeseburger by comparing image 1900 with images of cheeseburgers, it may determine that cheeseburger 1900 is a cheeseburger based on detection of the ingredients that make up cheeseburger 1902. In this example, wearable apparatus 110 may determine that an image of lettuce corresponds with a portion component 1906, an image of tomato corresponds with component 1910, and an image of sliced cheese corresponds with component 1908. Based on this incomplete identification, wearable apparatus 110 may determine that cheeseburger 1902 is neither lettuce, nor tomato, nor sliced cheese, but that it is something containing those ingredients. It is contemplated that the at least one processing device may then search for images of known consumable products containing the three determined ingredients and use those images for further comparison with image 1900. The comparisons may lead to a determination that cheeseburger 1902 is a cheeseburger. Alternatively, the comparisons may lead to further identification of ingredients. For example, the at least one processing device may determine that component 1912 is a meat patty, component 1904 is a top bun, and component 1914 is a bottom bun. The process of identifying ingredients and using those ingredients to generate a set of images to compare with the detected consumable product helps determine the type of a consumable product.

It is contemplated that the at least one processing device may be configured to use a neural network to determine a type of product from a list of determined ingredients. For example, the neural network may include a first layer configured to receive a plurality of ingredients, at least one hidden layer, at an output layer configured to identify the most likely type of consumable product associate with the ingredients. For example, if the input to the neural network includes the list of lettuce, tomato, sliced cheese, and meat patty, the output from the neural network would be a proper identification of cheeseburger 1902 as a cheeseburger.

It is also contemplated that if a type of the consumable product may not be directly determined by the image analysis, the identification of ingredients may be used to determine feedback related to the consumable product, as discussed further below. It is also contemplated that the at least one processing device may be configured to seek input from user 100 when ingredients are identified but not an ultimate type of the consumable product. For example, the at least one processing device may generate instructions for causing a device to display image 1900 and the list of ingredients including lettuce, tomato, sliced cheese, and meat patty, and to request input form user 100 regarding the proper type. A device may then be configured to perform the operations of the instructions and to receive the input. The input may then be saved with the image, e.g. image 1900, for later use in comparison to other captured images.

It is further contemplated that the at least one processing device may be configured to determine the ingredients of a consumable product after the type of the product has been determined. Identification of ingredients may be accomplished by comparison of the determined consumable product with known consumable products of the same type, wherein the known consumable products have varying ingredients. For example, if wearable apparatus 110 determined that cheeseburger 1902 is a cheeseburger by comparing it with images of known cheeseburgers, it may perform further operations to determine the ingredients of cheeseburger 1902. In this example, the processing device may be configured to compare a plurality of images of cheeseburgers having different ingredients to image 1900. As an example, the processing device may compare image 1900 with an image of a cheeseburger having onion, a cheeseburger having no additional toppings, a cheeseburger having two meat patties, a cheeseburger having a turkey-based meat patty, a cheeseburger having a sesame-seed bun, a cheeseburger having a whole-wheat bun, and so forth. The ingredients making up cheeseburger 1902 may then be identified in substantially the same manner as described above. The ingredients that make up a consumable product may be used for determining feedback related to the consumable product, as described further below.

In some embodiments, the at least one processing device may be configured to determine the type indicator associated with the detected consumable product based, at least in part, on detection of a label associated with packaging of the consumable product and recognition of text appearing on the detected label. The text may be, for example, a logo, a description of the product, a name of the product, and so forth, for example, the image of the consumable product may contain a wrapper or other packaging associated with the consumable product. It is contemplated that the at least one processing device may be configured to identify the packaging and detect text thereon (e.g., using an OCR program) and use the text to determine the type of the consumable product. For example, the detected consumable product may be associated with a detected box that contains the text "Big Mac®" and wearable apparatus 110 may determine that the defected consumable product is a cheeseburger based on this information. Matching the text "Big Mac®" with the type "cheeseburger" may be accomplished in substantially the same manner as the image comparison described above. For example, an image known to contain a cheeseburger and also containing the words "Big Mac®" may be matched with the image of the detected consumable and the corresponding text may be used to determine that the detected consumable product corresponds with the known cheeseburger. It is also contemplated that wearable apparatus 110 may match the text "Big Mac®" with a cheeseburger by supplying the term "Big Mac®" as a keyword for a search query, as described above, and determining based on the search results that the detected consumable product is a cheeseburger. Additionally or alternatively, the processing device may be configured to determine the type without using image comparison. For example, the keyword search may return nutritional information or a description of a "Big Mac®," which is sufficient to determine the consumable product is a cheeseburger without requiring additional analysis.

In another example, the at least one processing device may be configured to use the text detected in an image as a keyword to determine the type of the detected consumable product. This may be advantageous when the text detected in the image is not directly associated with a consumable product type (e.g., the "Big Mac®" example above) but describes a quality or characteristic of the type of the consumable product. The keyword may be used to search for images of related consumable products, as described above, or otherwise used to determine a type of the consumable product. Using the keyword to search for images of known consumable products may reduce the pool of images used for comparison with a detected consumable product thereby reducing the processing time. For example, the at least one processing device may detect the word "Atlantic" in an image containing a detected consumable product, or in an image related to the image containing the detected consumable product, and per form a search for images of consumable products associated with the word "Atlantic." The images returned from the search may include various seafood products sourced from the Atlantic Ocean, which may be compared with the image of the detected consumable product as described above, to determine a type of the detected consumable product. In other examples, the detected word may be related to a common descriptor of types of consumable products, such as "spicy," "juicy," "salty," "sweet," "savory," and so forth. It is contemplated that one or more keywords may be used in each search. Using more than one keyword may produce more relevant images of known consumable products and improve the likelihood of determining the type of the detected consumable product with fewer comparisons. xx In another example, wearable apparatus 110 may detect a menu from which user 100 orders a meal. It is contemplated that wearable apparatus 110 may additionally detect an indication of which menu option user 100 ordered, for example, by detecting audio of user 100 conveying the order to a server. Based on this information, wearable apparatus 110 may determine that a later detected consumable object is of the type ordered by user 100. For example, wearable apparatus 110 may capture an image of a menu at a first time and capture an image of a consumable product at a second time. Based on the menu and consumable product being captured in a similar location and in temporal proximity, the at least one processing device may determine that the consumable product corresponds with a product listed on the menu. In this example, the at least one processing device may compare the image of the detected consumable product with an image of each product listed on the menu to determine the type of the consumable product.

In some embodiments, the at least one processing device may use a combination of a keyword search and the image comparison to determine a type of consumable product. This may be advantageous when, for example, several types of consumable products have a similar visual appearance. For example, a comparison of an image of a detected consumable product with a plurality of images of known consumable products, as described above, may be effective for determining that a consumable product is, for example, a glass of milk. However, a glass of milk may have substantially the same appearance if it is whole milk or 2% milk. In this example, detection of a keyword, such as "whole" in a menu or ingredients list, or as a spoken word may be used in addition to the visual classification to determine that the detected consumable product is a glass of whole milk. The combined visual and textual or vocal identification described here may be particularly advantageous for distinguishing between consumable products of the same type having different ingredients or qualities, such as organic and non-organic produce, gluten-free and gluten-containing grains, original or fat-free products, grass-feed or corn-feed meats, and so forth. It is contemplated that the visual identification and the textual or vocal identification may be performed at substantially the same time or in any sequence.

Consistent with this disclosure, the at least one processing device may be configured to analyze one or more of the plurality of images to estimate an amount of the consumable product consumed by a user. The estimated amount may be measured as a volume, a percentage, a number of consumption events, and so forth. For example, if the type of the consumable product is a food, the estimated amount may be a number of spoonfuls, handfuls, units, bites, or the like. In another example, if the type of the consumable product is a beverage or drink, the estimated mount may be volume, a number of sips, glasses, bottles, cans, or the like. In another example, if the type of the consumable product is a drug, the estimated amount may be a number of pills, injections, sips, or the like. In another example, if the type of the consumable product is a cigarette, the estimated amount may be a number of puffs, cigarettes, cartons, or the like. It is contemplated that the estimated amount may be any other quantifier of a consumable product and may vary depending on the type of the consumable product.

In some embodiments, the estimated amount of a consumable product consumed may be determined by comparing the amount of consumable product detected at a first time with an amount detected at a second time. The amount present at each time period may be represented as a dimension of the consumable product, a number of items of the consumable product, a percentage of the consumable product, or the like. For example, if wearable apparatus 110 captures image 1800, the amount of broccoli 1806 present may be represented as 13 broccoli crowns, the amount of steak 1804 present maybe represented as 5.5 inches wide by 8.5 inches long and 1.25 inches thick, the amount of wine 1816 present may be represented as 100% of a traditional wine-pour, and so forth. The amount of consumable product present at a second time may be similarly detected and the amount consumed by a user may be determined by calculating the difference between the amount present at the first time and the amount present at the second time. Continuing the example, later during a meal, wearable apparatus 110 may capture an image substantially similar to image 1800 and detect an amount of each consumable product present at the second time. For example, the amount of broccoli 1806 present at the second time may be represented as 5 broccoli crowns, the amount of steak 1804 present may be represented as 2.5 inches wide by 3 inches long by 1.25 inches thick, the amount of wine 1816 present may be represented as 20% of a traditional wine-pour, and so forth. The at least one processing device may then estimate the amount of each consumable product consumed. For example, the amount of broccoli 1806 consumed may be represented as eight broccoli crowns, the amount of steak 1804 consumed may be represented as 3 inches wide by 5.5 inches long by 1.25 inches thick, the amount of wine 1816 consumed may be represented as 80% of a traditional wine-pour, and so forth. The at least one processing device may perform additional operations to estimate the amount of consumable product consumed in a different unit of measure. For example, the measurements of steak 1804 consumed (i.e., 3 inches wide by 5.5 inches long by 1.25 inches thick) may be compared to a graph, chart, or other source to determine how many ounces of steak 1804 were consumed. The graph, chart, or other source may be accessed through a search in substantially the same manner as described above in relation to the keyword searches.

In some embodiments, the amount of consumable product consumed by a user may additionally or alternatively be calculated based on a comparison of the consumable product with another consumable product or a non-consumable product. For example, rather than comparing the amount of steak 1804 present at a first time with the amount of steak 1804 present at a second time to determine the amount of steak 1804 consumed, the at least one processing device may compare steak 1804 with plate 1802 at each time period. The dimension of plate 1802 serves as a constant and may be a more effective point of comparison for estimating a consumed amount. For example, steak 1804 may occupy 35% of plate 1802 in image 1800 and may occupy 15% of plate 1802 in an image substantially similar to image 1800 captured at a second time. The at least one processing device may then use the dimensions of plate 1802 to determine an amount of steak 1804 consumed. This may be a particularly effective means for estimating the amount of consumable product consumed when the consumable product depends upon another object for its dimension. For example, the amount of wine 1816 consumed may be best determined by comparing the amount of wine 1816 present at a first time with wine glass 1814 and comparing the amount of wine 1816 present at a second time with the same wine glass 1814. It is further contemplated that the consumable product may be compared to an object unrelated to consumption to determine the amount consumed. For example, the pile of mashed sweet potatoes 1808 may be compared to candle 1824 at both the first and second time period.

Consistent with this disclosure, the at least one processing device may be configured to analyze a plurality of images captured in sequence to estimate an amount of consumable product consumed. For example, wearable apparatus 110 may be configured to capture an image in response to every consumption indicator, as described above, and capture a series of images related to a single consumption event, such as a meal. For example, an image may be captured each time a user's hand approaches the mouth of the user, or another consumption indicator occurs.

In some embodiments, the estimated amount of consumable product consumed may be calculated as a number of bites, sips, spoonfuls, handfuls, pieces, pills, or other unit. The number of units consumed may be determined by any means consistent with this disclosure. For example, wearable apparatus 110 may be configured to capture an image in response to each consumption indicator, as discussed above, and the number of units may be calculated by counting the number of limes user 100 brought a unit of consumable product to his or her mouth. In another example, wearable apparatus 110 may be configured to capture an image at an initial time and at a second time, as discussed above, and the number of units consumed may be calculated based on the estimated amount consumed and a known or determined average unit size.

In some embodiments, the at least one processing device may be configured to access a database to determine the standard or recommended serving size for a type of consumable product and determine the amount of consumable product consumed as an amount of servings consumed. A standard or recommended serving size is often expressed in standard units, such as units, grains or ounces, and information relating thereto is readily available online. For example, a keyword search performed as described above may locate information relating to a standard serving size. The at least one processing device may then determine the amount of consumable product as a function of the standard serving size. For example, if the standard serving size of a consumable product is 4 ounces and the processing device determines the user consumed 6 ounces of the consumable product, the processing device may determine that the user consumed 1.5 servings of the consumable product.

It is contemplated that one or more of the several methods of estimating an amount of consumable product consumed by a user may be performed at substantially the same time or that they may be performed in any combination. For example, the at least one processing devices may directly compare the dimension of a consumable product present at a first time with the dimension of the consumable product present at a second time and compare the dimension at each time to the dimension of one or more other objects. For example, the image 1800 captured at a first time may be analyzed to determine the dimension of steak 1804 and plate 1802 and a later image substantially similar to image 1800 may be analyzed to determine the remining dimension of steak 1804 and the dimension of plate 1802. This may allow for a more precise comparison because the image captured at the second time may be modified such that the dimension of plate 1802 is the same at each time period, thereby ensuring that the dimension of steak 1804 at the second time directly corresponds with the dimension of steak 1804 at the first time. Other combinations are possible, and this example is not limiting.

It is contemplated that the at least one processing device may use non-consumable products or objects to facilitate comparison of a first and second image of a consumable product when determining the amount of consumable product consumed. For example, when comparing an image of a consumable product captured at a first time and an image of a consumable product captured at a second time, a non-consumable product present in each image may be used to modify either the first or second image to allow for direct comparison between the two images. For example, image 1800 may be captured at a first time and a second image may be captured at a second time. The second image may contain all or most of the products present in image 1800, but may have been captured from a different angle or distance or under different conditions. If both images contain candle 1824 and table edge 1832, the at least one processing device may tilt, zoom, crop, or otherwise modify the second image until, for example, candle 1824 is of the same size in each image and table edge 1832 is in a similar position in each image. Once the second image has been modified, the amount of consumable product may be estimated as described above.

Consistent with this disclosure, the at least one processing device may be configured to analyze for plurality of images to estimate a rate at which the detected consumable product is consumed by the user. The rate of consumption may be presented as a function of any amount of consumable product consumed over any period of time in which the consumption occurred. It is contemplated that the rate of consumption may be estimated at substantially the same time as the amount of consumable product consumed is calculated. For example, when the amount is determined by comparing an amount of consumable product present in an image captured at a first time with the amount of consumable product present at a second time, as described above, the rate of consumption may be calculated by dividing the determined amount by the difference between the first and second time. In another example, when the amount is determined as a number of units consumed, as described above, the rate of consumption may be determined by dividing the number of units by the difference between the first and second time.

Consistent with this disclosure, the at least one processing device may be configured to determine a feedback based on the on the detected consumable product. The feedback may include visual feedback, audible feedback, tactile feedback, a combination thereof, or the like. The feedback may include any information of interest to a user. The feedback may include any information generated or obtained by the at least one processor by any means disclosed above. The at least one processing device may generate instructions for causing the feedback to be outputted to a user. The instructions may be generated by, for example, processor 210 in wearable apparatus 110, processor 540 in computing device 120, an external processing device, or a combination thereof. The feedback may include any combination of audible, visible, or tactile feedback. In some embodiments, the feedback may be output by feedback outputting unit 230. For example, the instructions generated by processor 210 or processor 540 may be received by feedback outputting unit 230 and feedback outputting unit 230 may be configured to provide the feedback to user 100.

In some embodiments, the feedback may be output by wearable device 110. For example, the feedback may include tactile feedback, and wearable apparatus 110 may be configured to vibrate in response to receiving the instructions. In another example, the feedback may include audible feedback and wearable apparatus 110 may be configured to perform the feedback, for example, by playing it over a speaker or through headphones. In another example, the feedback may be visual feedback and wearable apparatus 110 may be configured to display the feedback, for example, on a display in wearable apparatus 110 or by displaying the feedback on lens of glasses 130. If the feedback is tactile feedback, apparatus 110 may be configured to vibrate when it is determined that the user has consumed a predetermined amount of one or more consumable, has received a predetermined amount of a nutrient, or the like. In some embodiments, the feedback may be output by computing device 120. For example, computing device 120 may be configured to vibrate or perform audible feedback when it receives the feedback instructions from wearable apparatus 110 and or another device (e.g., a remote server), in another example, computing device 120 may be configured to display the feedback, for example, by displaying visual feedback on display 260).

In some embodiments, causing the feedback to be output may include transmitting the feedback to a device paired with the wearable apparatus. The device may include any device disclosed herein or any other device capable of outputting the feedback. For example, the device may include one of a smartphone, a tablet, or a smartwatch. It is contemplated that an application installed on the device may be configured to receive the instructions and cause the feedback to be output. The feedback or the instructions for causing the feedback to be output may be transmitted to the device by any means, for example, via WiFi over a network, via the Internet, via Bluetooth®, etc.

The feedback may relate to a consumable product or a type thereof. For example, if the ingredients of a consumable product are determined as described above, the feedback may include information relating to one or more ingredients. For example, after consumption of cheeseburger 1902, the feedback may include: "you consumed a cheeseburger, which contained, a bun, a meat-patty, lettuce, two tomatoes, and one slice of cheese." For example, the feedback may include the identity of the type of consumable product or the estimated amount of consumable product consumed. For example, after analyzing image 1900, the at least one processing device may provide visual feedback including, "you consumed a cheeseburger." The feedback may include additional information related to the consumable, such as the location or time at which the consumable product was consumed. For example, the feedback may include "you consumed a cheeseburger at 12:15 PM."

In some embodiments, the feedback may be based on a type of the detected consumable product and an estimated amount of the consumable product consumed by a user. The type of the detected product and the amount consumed may be determined by any means disclosed herein. The feedback may include an identifier of the type of consumable product and the amount of consumable product consumed. For example, after analyzing image 1800 as described above, the at least one processing device may provide feedback including: "you consumed 8 broccoli crowns" or "you consumed 2 glasses of wine." In some embodiments, the feedback may be based on the estimated rate at which the detected consumable product is consumed. For example, the at least one processing device may determine a rate of consumption as described above and may use data related to the rate to determine a feedback. The feedback may be determined by comparison to user preferences, established standards, of the like or may include a general description of the rate. For example, feedback based on a rate may include: "you consumed 3 alcoholic drinks in 2 hours" or "you consumed 2,500 calories in 1 day, the recommended daily caloric intake is 2,000 calories" or the like.

In some embodiments, the feedback may include data derived from information generated by the at least one processing device. The derived data may, for example, use information relating to the type and amount of consumable product consumed to determine information of interest to a user. The at least one processing device may be configured to access values stored on a database, network, Internet, intranet, or device and use that data to determine the feedback. For example, the feedback may be determined based on values stored for the detected consumable product. The values may include nutritional values, recommended values, or other values related to consumption, such as the amount of calories, carbohydrates, fat, proteins, vitamins, micronutrients, alcohol, nicotine, or the like associated with the consumable product. For example, upon determining that consumable product 1804 is a steak, the at least one processing device may search for nutritional values for steak 1804 and the feedback may include the nutritional information. For example, the feedback may include: "you consumed a steak, which has 61 calories, 4 grams of fat, 0 grams of carbohydrates, and 5.7 grams of protein per serving." Additionally or alternatively, the amount of consumable product may be used to determine further feedback, such as an estimation of consumed calories, consumed carbohydrates, consumed fat, or consumed protein. Continuing the above example, the amount of steak 1804 consumed may be used to determine how many servings user 100 consumed, as described above, and the feedback may include: "you consumed 1.5 servings of steak, which includes 91.5 calories, 6 grams of fat, 0 grams of carbohydrates, and 8.6 grams of protein" or "you consumed 91.5 calories, 6 grams of fat, and 8.6 grams of protein" or the like. In a similar example, the consumed product may be an alcoholic drink and the feedback may relate to an amount of consumed alcohol. For example, the at least one processing device may search for the alcohol content for a type of product and use that information to determine a total amount of alcohol consumed. The feedback determined in this example may include: "you consumed 4 glasses of wine," "you consumed 4 glasses of Merlot, which is 14.5% alcohol," or the like.

In some embodiments, the determined feedback may include a comparison to a recommended amount of consumable product. A recommended amount may be an amount included in for example, a typical 2,000 calorie diet, a recommended number of servings for a category of food, a surgeon general's alcohol safety warning, a medical association's recommended daily intake, and so forth. For example, in the example above, the nutritional information for steak 1804 may include a percentage breakdown of the recommended daily intake of each nutrient or the at least one processing device may be configured to determine a percent daily value. For example, the feedback related to steak 1804, as disclosed above, may include: "you consumed 91.5 calories, which is 4.6% of the recommended 2,000 calorie diet." In another example, the feedback determined for wine 1816, as disclosed above, may include; "you consumed 4 glasses of Merlot, the World Health Organization recommends consumption of no more than 2 alcoholic drinks a day."

In some embodiments, the feedback may include information relating to a comparison between the determined consumption and user preferences relating to consumption. A user may set goals related to consumption, such as goals intended to aid them in losing or gaining weight, quitting smoking, drinking fewer alcoholic drinks a day, and so forth. It is contemplated that wearable apparatus 110 and/or computing device 120 may be configured to receive and store user preferences, for example in memory 550 andor 550*b*. The at least one processing device may then compare the determined amount and/or type of consumable product with the user preferences to determine a feedback. For example, a user preference may indicate that user 100 desires to consume less than 150 grams of carbohydrates per day. In this example, feedback may include a message containing, "you consumed 100 grams of carbohydrates, which is 66% of your daily goal."

In some embodiments, the feedback of the instructions for generating the feedback may be transmitted to one or more devices. For example, the feedback may be transmitted to a first device for storage as described above and transmitted to a second device for outputting to a user. In some embodiments, the feedback may be transmitted to a server, such as server 250. The feedback may be transmitted by, for example, wireless transceiver 530 in wearable apparatus 110.

In some embodiments, feedback or the instructions for generating the feedback may be stored. For example, at least one processing device may be configured to store the feedback in a memory device. The memory device may be any memory device in communication with the processing device, such as memory 550, 550*b*, a database, or another memory device. The stored feedback may include at least one value that is aggregated over time. The value that is aggregated over time may be any that is of interest to a user, as defined by user preferences, or any that is determined to be of importance. For example, the at least one value may relate to a number of calories consumed by the user over a particular time period, an amount of alcohol consumed over a particular lime period, a number of pills consumed over a particular time period, or the like. The time period may be, for example, one or more hours, one or more days, one or more weeks, one or more months, and so forth.

Stored feedback may be used to determine additional feedback or future feedback. In some embodiments, the stored feedback may include information relating to the captured image underlying the feedback and may be used in a later determination of a type or amount of consumable product consumed by a user. For example, a captured image may be compared with an image associated with the stored feedback, as described above, and the at least one processing device may determine that the captured image contains the same consumable product as the image associated with the stored feedback. The at least one processing device may, based on the determination, further determine that feedback substantially similar to the stored feedback is appropriate for the captured image. In some embodiments, the stored feedback may be used to detect patterns, trends, or other information and provide additional feedback related to the information. For example, the stored feedback may include one or more aggregated values, as described above, and the at least one processing device may compare the aggregate values to user preferences, recommended intake values per day or another time period, predetermined values, or other metrics to generate additional feedback. For example, the aggregated value may relate to total calories consumed in a particular time period and the additional feedback may include an indication of how the value compares to a user's caloric intake goals as defined by a user preference. In another example, the at least one processing device may compare the aggregate value for a first time period with the aggregate value for a second time period and generate feedback based on the comparison. For example, it is contemplated that, at the end of each week, the processing device may compare an aggregate value for that week with a related aggregate value for the proceeding week or weeks and provide feedback relating to the comparison. The feedback man include, for example, "this week you consumed 1,321 fewer calories than you consumed last week" or "last week you consumed 15,759 calories; this week you consumed 14,438" or the like. It is contemplated that the feedback may include a graphic representation of the comparison, such as, for example, a pic graph, line graph, bar chart, table, or other representation of the relationship between the values corresponding with a plurality of time periods.

In some embodiments, feedback may be generated in response to a user input requesting information related to consumption. For example, a user may request information relating to a consumable product (e.g., the nutritional values related thereto, the amount consumed, the rate of consumption, etc.), to a consumption event (e.g., a meal, snack, bite, etc.), a time frame (e.g., consumption over an hour, day, week, etc.), a combination thereof, or any other information related to consumption. The feedback may then be generated as disclosed herein or, if previously generated, accessed from a storage device as discussed above. It is contemplated that a user may request feedback on an ad hoc basis or may, through a user preference, request feedback on a set schedule. For example, one or more user preferences may indicate that user 100 desires feedback substantially continuously (e.g., as a consumable product is consumed); only when consumption inconsistent with a user preference is determined (e.g., when the processing device determines the user consumed too many calories, drinks, carbohydrates, etc.); after every meal, day, week, month, or other time frame; or when any other condition is met. It is further contemplated that a user may dictate the type of feedback he or she wishes to receive. For example, user 100 may, on an ad hoc basis or through user preferences, dictate that he or she wishes to receive feedback containing a comparison of the consumption occurring between a first and second time frame, a comparison of a consumption event with user preferences, a nutritional breakdown of a consumable product, and so forth.

In some embodiments, the at least one processing device may be configured to determine a type of feedback a user wishes to receive and to provide that feedback. For example, if user 100 requests a particular type of feedback, as described above, under the same or similar conditions one or more times, the processing device may automatically generate and provide that type of feedback when those conditions are present. For example, if user 100 request feedback between 9 PM and 10 PM and request that the feedback contain a daily breakdown of consumed nutrients, the processing device may, absent a subsequent request, begin automatically providing a daily breakdown of consumed nutrients between 9 PM and 10 PM. It is also contemplated that rather than automatically providing feedback consistent with a detected pattern or trend, the at least one processing device may provide feedback relating to the detected pattern or trend. Continuing the example, rather than automatically providing a daily breakdown of consumed nutrients, the at least one processing device may provide an output prompting the user to include the daily breakdown in his or her user preferences.

In some embodiments, the processing device may be configured to provide feedback before consumption. For example, the feedback may be provided as soon as the consumable product is detected. In this example, the feedback may include an indication of the nutritional value of the detected consumable products. As an example, if wearable apparatus 110 captures image 1800, it may provide feedback relating to the calories, fat, protein, carbohydrates, and other nutritional value for each of steak 1804, broccoli 1806, mashed sweet potatoes 1808, dessert 1822, wine 1814, and the like. The feedback may be displayed to user 100 by any means disclosed herein. Displaying the feedback as part of a head-up augmented reality display may be particularly advantageous for this embodiment because it enables user 100 to visualize the nutritional implications of his or her dietary choices.

Consistent with this disclosure, the at least one processing device may determine a recommendation based on the monitored consumption. The recommendation may be provided to a user 100, for example, as part of the feedback provided to a user as described above. For example, the feedback may include a recommendation associated with the detected consumable product. The recommendation may include any information related to the consumable product, to one or more user preferences, to one or more health standards, and so forth.

Figure 20:
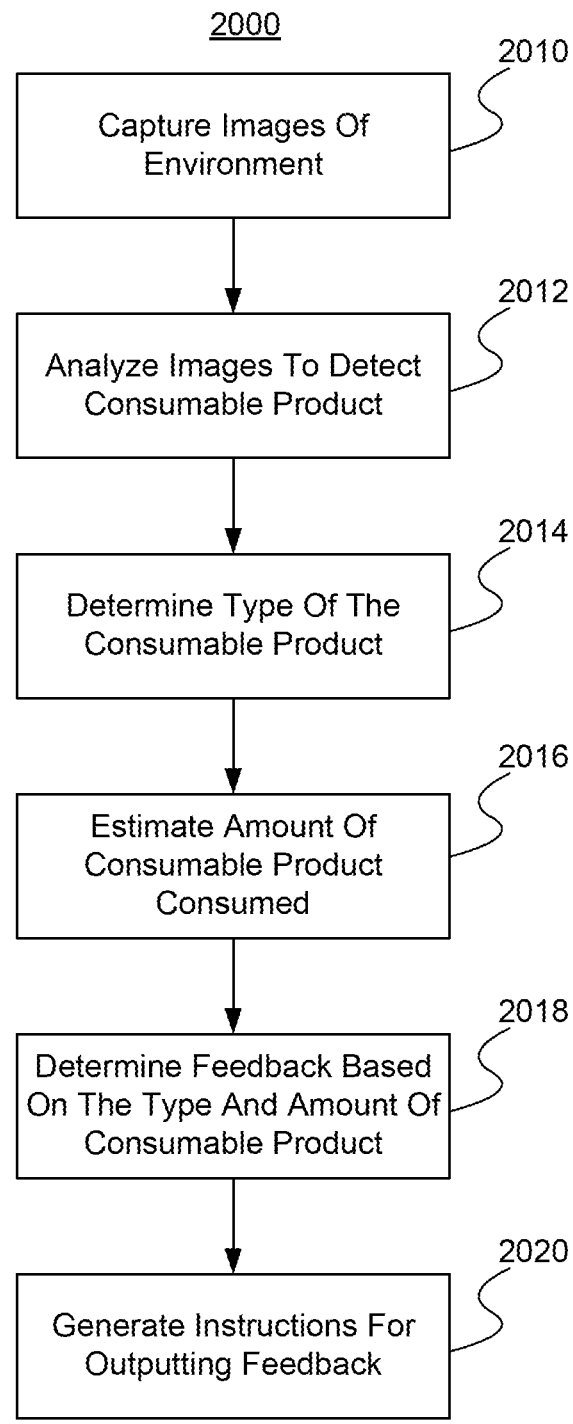
FIG. 20 is a flowchart of a method for monitoring consumption of a user according to a disclosed embodiment consistent with the present disclosure.

FIG. 20 is an exemplary flowchart of a method 2000 for automatically monitoring the consumption of a user and providing feedback relating to the consumption to a user. It is understood that method 2000 is exemplary only and the method performed by wearable apparatus 110 may be substantially similar to that of method 2000, may include only portions of method 2000, or may include additional steps not shown in method 2000. In some embodiments, the steps of method 2000 may be performed by wearable apparatus 110 and one or more external devices (e.g., a processor included in an external server that receives data from wearable apparatus 110 over a network and/or a processor included in an external device such as a laptop, smartwatch, smartphone, tablet, earphones, etc.). In other embodiments, method 2000 may be performed by a general-purpose computer or a special-purpose computer built according to embodiments of the present disclosure.

Method 2000 may include a step 2010 for capturing one or more inputs from an environment of a user. The input may be captured by a visual capture device, audio capture device, or other devices configured to capture images, videos, audio signals, or the like. For example, capturing the one or more images may include capturing one or more images from at least one image capture device of wearable apparatus 110. In some embodiments, the images may be part of a video stream.

Method 2000 may include a step 2012 for analyzing the captured images or videos to detect a consumable product represented in at least one of the captured images. The consumable product may be detected by any means disclosed herein. For example, image analysis as described above may be used to determine whether particular objects are consumable or other non-consumable objects. Further, the analysis may include determining through image analysis whether a consumable product was eaten and whether the person who ate the consumable product was a user of the wearable apparatus. For example, the images captured by the wearable apparatus may be analyzed to determine that a band holding a consumable product is a hand associated with the user of the wearable apparatus or that a plate of food or food packaging in an image is positioned in from of the user of the wearable apparatus.

Method 2000 may include a step 2014 for determining a type of the detected consumable product. The type of the detected consumable product may be determined by any means disclosed herein. For example, through image analysis, an identifier of the detected consumable product, such as a generic product name or a brand name may be determined as discussed above.

Method 2000 may include a step 2016 for estimating an amount of the consumable product consumed by the user. The amount of consumable product may be determined by analyzing the captured images, for example, by detecting an amount of consumable product present at a first time and detecting an amount of consumable product present at a second time, the difference between the two amounts representing the amount consumed by the user. In some embodiments, method 2000 may include a step (not shown) for estimating a rate at which the detected consumable product was consumed by the user. Still further, in some embodiments, the amount of consumable product may be determined by counting a quantity of the consumable product consumed by the user of the wearable apparatus (e.g., the user ate three pancakes and drank two cups of coffee).

Method 2000 may include a step 2018 for determining a feedback based on the type of consumable product consumed and the amount of the consumable product consumed. The feedback may include any feedback disclosed herein. In some embodiments, where method 2000 includes a determination of the rate of consumption, determining the feedback may include determining feedback based on the rate of consumption in addition to the amount and type of consumable product consumed. Method 2000 may include a step 2020 for generating instructions for causing the feedback to be output to the user. The feedback may be output by any means disclosed herein. Method 2000 may include a step (not shown) for transmitting the instructions. The instructions may be transmitted to a device and the device may output the feedback in response to receiving the instructions. The instructions may additionally or alternatively be transmitted to wearable apparatus 110 and wearable apparatus 110 may provide audible or visual feedback to the user in response to receiving the instructions. Method 2000 may include a step (not shown) for storing the determined feedback, the generated instructions, or data obtained or generated during any step of method 2000). Additional examples of feedback are discussed below.

Figure 21:
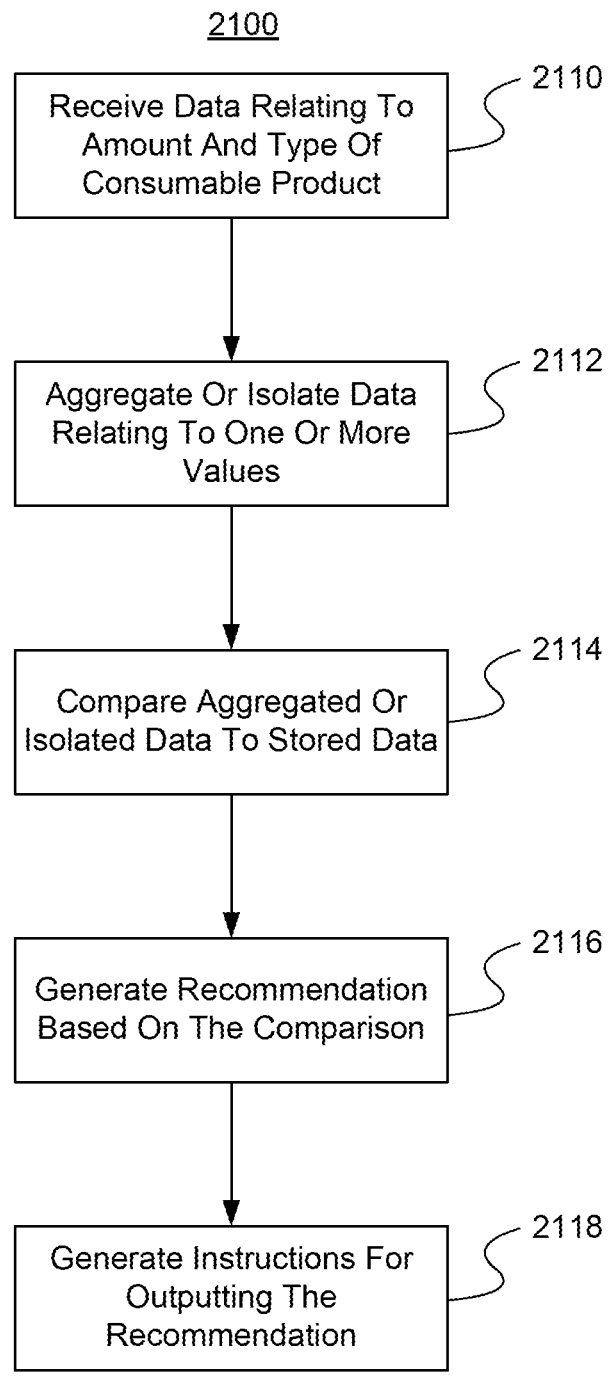
FIG. 21 is a flowchart of a process generating a recommendation consistent with the present disclosure.

FIG. 21 is an exemplary flowchart showing a process 2100 for determining a recommendation related to consumption. Process 2100 may include a step 2110 for receiving data relating to one or more of the type or amount of consumable product consumed. The data may be generated by the one or more processors as described above. The data may be received directly from one or more processor or may be accessed from a storage device or over a network.

Process 2100 may include a step 2112 lot aggregating or isolating one or more values in the data. For example, the data may be stored as described above and one or more values may be aggregated. The aggregation may include saving data related to a plurality of consumption events including the date, time, consumable product, amount consumed, rate of consumption, and so forth for each consumption event. In another example, the values in the data may be compared to other values, such as those in user preferences or health standards, and one or more values may be isolated based on, for example, exceeding an amount indicated in the user preferences or health standards. For example, if the data indicates that user 100 consumed 200 grams of carbohydrates and the user preferences associated with user 100 indicate that he or she intends to consume no more than 150 grams of carbohydrates a day, the 200 gram value may be isolated.

Process 2100 may include a step 2114 for comparing the aggregated or isolated data to stored data. The stored data may be, for example, guidelines, conditions, or rules for generating a recommendation. The stored data may be stored on a memory, such as memory 550, 550*b*, or on a database or other memory device. As an example, a stored rule may indicate that if a processing device determines that a value of a nutrient consumed by a user exceeds a threshold, then a recommendation should be generated and output. The stored data may reflect one or more recommendation rules. For example, a recommendation rule may dictate that if a user consumes a nutrient in an amount within a threshold of a predetermined value, that a recommendation should be generated. The comparison in this example, would comprise of a comparison between the amount of nutrient consumed and the predetermined value. The stored data may reflect a pattern determined or identified by the processing device. For example, the processing device may aggregate the data as discussed above and may determine one or more consumption habits of the user, such as a value of calories, pills, cigarettes, fats, protein, etc. that the user consumes on a routine basis or a time frame in which the user consumes the same. The comparison, in this example, comprises of a comparison between received data and the pattern. As may be appreciated from this disclosure, the stored data may reflect any rules, guidelines, patterns, or other information useful for determining a recommendation.

Process 2100 may include step 2116 for generating a recommendation based on the comparison. The recommendation may be generated in substantially the same manner as the instructions for causing the feedback to be output, as described above. One or more rules may dictate the content of the recommendation. For example, if the processing device determines that the user consumed more of a nutrient than is recommended by a health standard, a rule may dictate that the processing device recommend to the user that he or she consume less of that nutrient on a subsequent day. The recommendation may be generated in accordance with one or more rules or with a pattern detected by the processing device. For example, if user 100 consumes an apple every day, the processing device may recommend that user vary his or her consumption by, for example, consuming a pear or orange rather than an apple. The recommendation may be generated in accordance with one or more advertising criteria, which may be provided by an advertiser. For example, an advertising criteria may dictate that processing device recommend a product to every consumer who consumes a specific type of consumable product.

Process 2100 may include a step 2118 for generating instructions for outputting the recommendation. The instructions for outputting the recommendation may be generated in substantially the same manner disclosed with respect to generating the instructions for causing a device to output the feedback. The instructions may include an indication of how, when, and where a recommendation is to be output as well as the content of the recommendation. It is contemplated that the instructions may be transmuted to an output device, stored in a memory, or processed by an outputting unit or processing device.

In some embodiments, the recommendation may be provided prior to consumption of a detected consumable product. For example, wearable apparatus 110 may capture an image of a consumable product and the one or more processing devices may determine that the consumable product is of a first type as described above, prior to consumption of the consumable product, the processing device may provide a recommendation related to the type of consumable product. For example, if wearable apparatus 110 detects cheeseburger 1902, before user 100 begins eating, the at least one processing device may provide a recommendation related to cheeseburger 1902. The recommendation may include, for example, a recommendation that user 100 eat less than all of cheeseburger 1902. In another example, wearable apparatus 110 may detect a menu and provide a recommendation relating to what user 100 should order. For example, the at least one processing device may detect a menu and, in response, access stored data relating to what user 100 consumed prior to the detection of the menu. If, for example, user 100 consumed relatively unhealthy consumable products for breakfast and lunch, the at least one processing device may recommend that user 100 order a low-caloric or otherwise healthy option from the menu.

In some embodiments, the recommendation may include a recommendation to swap a consumable product that a user frequently consumed with a healthier alternative consumable product. For example, if the at least one processing device determines that user 100 consumes a soft-drink every day (by analyzing aggregated consumption data, for example), the at least one processing device may be configured to determine an alternative consumable product with similar characteristics to the soft-drink and recommend to user 100 that he or she replace the soft-drink with the alternative. In this example, the replacement product may be, for example, a diet soft-drink, a sports drink, a glass of water, a glass of tea, or the like. The at least one processing device may determine the healthier alternative by, for example, comparing the nutritional information of the detected consumable product with the nutritional information of one or more consumable products of the same type. The nutritional information may be accessed through a keyword search, as described above, or from a storage device in communication with the at least one processing device.

In some embodiments, the recommendation may include an advertisement. The advertisement may be provided to the at least one processing device by one or more advertisers. The advertisement may be provided to user 100 as a recommendation if the predetermined criteria is met. The predetermined criteria may be provided by an advertiser or determined by the at least one processing device, for example, the criteria may provide that if a certain brand of consumable product is detected, an advertisement from a different brand that provides the same or similar consumable product should be provided as a recommendation to user 100. For example, Coca-Cola® may provide an advertising criterion indicating that a Coke® advertisement should be displayed as a recommendation to user 100 whenever wearable apparatus 110 determined that user 100 consumed a Pepsi® product. It is contemplated that the advertisement criteria may include rules for providing an advertisement if any set of conditions is met.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A wearable apparatus for automatically monitoring consumption by a user of the wearable apparatus, by analyzing images captured from an environment of the user, the wearable apparatus comprising:
at least one image capture device configured to capture a plurality of images from an environment of the user of the wearable apparatus; and
at least one processing device configured to:
analyze the plurality of images to detect a consumable product represented in at least one of the plurality of images;
based on the detection of the consumable product represented in at least one of the plurality of images, analyze one or more of the plurality of images to determine a type indicator associated with the detected consumable product;
analyze the one or more of the plurality of images to estimate an amount of the consumable product consumed by the user;
analyze the one or more of the plurality of images to estimate a rate at which the detected consumable product is consumed by the user;

determine a feedback based on the type indicator of the detected consumable product, the estimated amount of the consumable product consumed by the user, and the estimated rate at which the detected consumable product is consumed by the user; and cause the feedback to be outputted to the user.

2. The wearable apparatus of claim 1, wherein the type indicator associated with the detected consumable product is at least one of food, beverage, alcoholic drink, pill, cigarette, or cigar.

3. The wearable apparatus of claim 1, wherein the type indicator associated with the detected consumable product is at least one of soup, salad, pasta, bread, cake, dessert, vegetable, or meat.

4. The wearable apparatus of claim 1, wherein the at least one processing device is configured to determine the type indicator associated with the detected consumable product based, at least in part, after detection of a label associated with packaging of the consumable product and recognition of at least a portion of text appearing on the detected label.

5. The wearable apparatus of claim 1, wherein the type indicator of the detected consumable product is food and the estimated amount is a number of bites, spoonfuls, handfuls, or units.

6. The wearable apparatus of claim 1, wherein the type indicator of the detected consumable product is beverage or drink and the estimated amount is a number of sips.

7. The wearable apparatus of claim 1, wherein the feedback provides an estimation of consumed calories, consumed carbohydrates, consumed fat, or consumed protein.

8. The wearable apparatus of claim 1, wherein the feedback relates to an estimation of an amount of consumed alcohol.

9. The wearable apparatus of claim 1, wherein the type indicator of the detected consumable product is determined by comparing at least a portion of the one or more of the plurality of images to stored images of consumable product types.

10. The wearable apparatus of claim 1, wherein the feedback is determined based on values stored for the detected consumable product.

11. The wearable apparatus of claim 1, wherein the feedback includes a recommendation associated with the detected consumable product.

12. The wearable apparatus of claim 1, wherein the feedback includes audible feedback or visual feedback.

13. The wearable apparatus of claim 1, wherein the feedback is stored in a memory device.

14. The wearable apparatus of claim 13, wherein the feedback stored in the memory device includes at least one value that is aggregated over time.

15. The wearable apparatus of claim 14, wherein the at least one value relates to calories consumed by the user over a particular time period.

16. The wearable apparatus of claim 14, wherein the at least one value relates to an amount of alcohol consumed by the user over a particular time period.

17. The wearable apparatus of claim 14, wherein the at least one value relates to a number of pills consumed by the user over a particular time period.

18. The wearable apparatus of claim 1, wherein causing the feedback to be output includes transmitting the feedback to a device paired with the wearable apparatus.

19. The wearable apparatus of claim 18, wherein the paired device includes one of a smartphone, a tablet, or a smartwatch.

20. The wearable apparatus of claim 1, wherein the at least one image capture device is a video camera.

21. A method for automatically monitoring consumption by a user of a wearable apparatus, the method comprising:

capturing, by the wearable apparatus, one or more images from an environment of the user;

analyzing the images to detect a consumable product represented in at least one of the one or more images;

determining a type of the detected consumable product;

analyzing the images to estimate an amount of the consumable product consumed by the user;

analyze the one or more of the plurality of images to estimate a rate at which the detected consumable product is consumed by the user;

determining a feedback based on the type of the consumable product, the amount of the consumable product consumed by the user, and the estimated rate at which the detected consumable product is consumed by the user; and generating instructions for causing the feedback to be output to the user.

22. The method of claim 21, wherein determining the feedback comprises determining a recommendation related to the consumable.

23. The method of claim 21, wherein determining the type of the consumable product comprises comparing the one or more images to stored images of consumable product types.

24. The method of claim 21, wherein determining the type of the consumable product comprises detecting a label associated with packaging of the consumable product and identifying at least a portion of text appearing on the detected label.

25. The method of claim 21, wherein analyzing the images to estimate the amount of the consumable product consumed by the user comprises determining a number of bites, spoonfuls, handfuls, units, sips, or pills consumed by the user.

26. The method of claim 21, wherein determining the feedback comprises comparing the amount of the consumable product consumed by the user with a stored amount for the type of consumable product and generating a recommendation based on the comparison.

27. The method of claim 21, further comprising: transmitting the instructions to a device to cause the device to display the feedback.

28. The method of claim 21, further comprising: storing the feedback in a memory device.

* * * * *